United States Patent [19]
Hoard et al.

[11] Patent Number: 6,143,909
[45] Date of Patent: Nov. 7, 2000

[54] SELECTIVE EPOXIDATION PROCESS FOR PREPARING PHARMACEUTICAL COMPOUNDS

[75] Inventors: David Warren Hoard, Greenwood; Eric David Moher, Indianapolis, both of Ind.; Vinod Francis Patel, Waltham, Mass.; Bryan Hurst Norman, Indianapolis, Ind.

[73] Assignee: Eli Lilly and Company, Indianapolis, Ind.

[21] Appl. No.: 09/380,005

[22] PCT Filed: Feb. 25, 1998

[86] PCT No.: PCT/US98/03667

§ 371 Date: Aug. 24, 1999

§ 102(e) Date: Aug. 24, 1999

[87] PCT Pub. No.: WO98/38164

PCT Pub. Date: Sep. 3, 1998

Related U.S. Application Data

[60] Provisional application No. 60/039,114, Feb. 26, 1997, and provisional application No. 60/039,116, Feb. 26, 1997.

[51] Int. Cl.$^7$ .................. C07D 303/38; C07D 301/02
[52] U.S. Cl. ........................... 549/549; 549/519
[58] Field of Search ..................... 549/519, 549

[56] References Cited

U.S. PATENT DOCUMENTS

| | | | |
|---|---|---|---|
| 4,845,085 | 7/1989 | Sesin | 31/395 |
| 4,845,086 | 7/1989 | Sesin | 31/395 |
| 4,868,208 | 9/1989 | Sesin et al. | 514/475 |
| 4,946,835 | 8/1990 | Hirsch et al. | 514/183 |
| 5,256,802 | 10/1993 | Macke et al. | 549/519 |
| 5,843,992 | 12/1998 | Nomura et al. | 514/475 |
| 5,998,637 | 12/1999 | Furui et al. | 549/518 |
| 6,025,506 | 2/2000 | Kaptein et al. | 549/519 |
| 6,103,666 | 1/2000 | Jew et al. | 514/475 |

FOREIGN PATENT DOCUMENTS

| | | |
|---|---|---|
| WO 95/17093 | 12/1994 | WIPO . |
| WO 96/40184 | 3/1996 | WIPO . |
| WO 96/39829 | 6/1996 | WIPO . |
| WO 97/07798 | 8/1996 | WIPO . |
| WO 97/08334 | 8/1996 | WIPO . |
| WO 97/23211 | 12/1996 | WIPO . |
| WO 98/08505 | 8/1997 | WIPO . |
| WO 98/08506 | 8/1997 | WIPO . |
| WO 98/08829 | 8/1997 | WIPO . |

OTHER PUBLICATIONS

Russell A. Barrow, et al., Total Synthesis of Cryptophycins. Revision of The Structures of Cryptophycins A and C. *J. Am. Chem. Soc.* (1995), 117, 2479–2490.

Robert E. Schwartz, et al. Pharmaceuticals From Cultured Algae. *Journal of Industrial Microbiology,* 5 (1990) 113–123.

Motomasa Kobayashi, et al. A total synthesis of Arenastatio A, an extremely potent cyctotoxic eepsipeptide, from the Okinawan marine sponge *Dysidea Arenaria, Chem. Pharm. Bull.* (1994) 42 (11); 2394–2396.

Charles D.Smith, et al., Cryptophycin: A new Antimicrotubule Agent Active Against Drug–Resistant Cells. *Cancer Research* 54, 3779–3784, Jul. 15, 1994.

Golakoti Trimurtulu, et al., Total Structures of Cryptophycins, Potent Antitumor Depsipeptides from the Blue–Green Alga Nostoc SP. Strain GSV 224. *J. Am. Chem. Soc.* 1994, 116, 4729–4737.

Kristen Kerksiek, et al., Interaction of Cryptophycin 1 With Tubulin and Microtubules. *FEBS Letters* 377 (1995) 59–61.

Motomasa Kobayashi, et al. Improved Total Synthesis and Structure–Activity Relationship of Arenastatin A, A Potent Cytotoxic Spongean Depsipeptide. *Chem. Pharm. Bull* 43 (9) 1598–1600 (1995).

Trimurtulu Golakoti, et al. Structure Determination, Conformational Analysis, Chemical Stability Studies, and Antitumor Evaluation of the Cryptophycins. Isolation of 18 new Analogs From Nostoc SP. Strain GSV 224. *J. Am. Chem. Soc.,* 1995, 117, 12030–12049.

Ruoli Bai, et al. Characterization of The Interaction of Cryptophycin 1 With Tubulin: Binding in The Vinca Domain, Competitive Inhibition of Dolastatin 10 Binding, and an Unusual Aggregation Reaction. *Cancer Research* 56, 4398–4406, Oct. 1, 1996.

Gregorz M. Salamonczyk, et al. Total Synthesis of Cryptophycins via A Chemoenzymatic Approach. *J. Org. Chem.,* 1996, 61, 6893–6900.

Rabindra Rej, et al. total synthesis of cryptophycins and their 16–(3–phenylacryloyl) derivatives. *J. Org. Chem.* 1996, 61, 6289–6295.

Richard E. Moore, et al. The Search for New Antitumor Drugs From Blue–Green Algae. *Current Pharmaceutical Design,* 1996, 2, 317–330.

T.H. Corbett, et al. Preclinical Anticancer Activity of Cryptophycin–8. *Journal of Experimental Therapeutics and Oncology,* vol. 1, No. 2, Mar. 1996, pp. 95–108.

Syed M. Ali, et al. Formal Syntheses of cryptophycin A and Arenastatin A. *Tetrahedron Letters,* vol. 38, No. 10, pp. 1703–1706, 1997.

Gottumukkala V. Subbaraju, et al., Three New Cryptophycins from Nostoc SP. GSV 224, *J. Nat. Prod.,* 1997, 60, 302–305.

*Primary Examiner*—Deborah C. Lambkin
*Attorney, Agent, or Firm*—John H. Engelmann

[57] ABSTRACT

Cryptophycin compounds possessing a β-epoxy moiety may be made with high stereoselectivity at various steps in the overall synthetic process. This invention also provides novel intermediates useful in preparing Cryptophycin compounds.

40 Claims, No Drawings

SELECTIVE EPOXIDATION PROCESS FOR PREPARING PHARMACEUTICAL COMPOUNDS

Provisional Application No. 60/034,114 Feb. 26, 1997.
Provisional Application No. 60/034,116 Feb. 26, 1997.
This appln is a 371 of PCT/US98/03667 Feb. 25, 1998.

BACKGROUND OF THE INVENTION

Neoplastic diseases, characterized by the proliferation of cells not subject to the normal control of cell growth, are a major cause of death in humans and other mammals. Clinical experience in cancer chemotherapy has demonstrated that new and more effective drugs are desirable to treat these diseases. Such clinical experience has also demonstrated that drugs which disrupt the microtubule system of the cytoskeleton can be effective in inhibiting the proliferation of neoplastic cells.

Cryptophycin compounds can now be prepared using a total synthetic process; however, many of the useful cryptophycin compounds contain a labile epoxide group. Barrow, R. A. et al., *J. Am. Chem. Soc.* 117, 2479 (1995). Applicants have discovered that the beta-epoxide can be particularly desired. However, in the Barrow et al. synthesis of some of the cryptophycin compounds of formula (I) below, the epoxidation is performed in the last step which provides only a 2:1 selectivity for the desired epoxide. Furthermore, the diastereomers are difficult to separate at this stage. While it would be desirable to epoxidize an earlier intermediate in the process, epoxides are sensitive to a number of reaction conditions. Moreover, there remains a need for processes with greater stereoselectivity to avoid difficult diastereomeric separations.

The present invention provides a much desired novel and efficient method for preparing cryptophycin compounds having an epoxide functionality. The epoxidation is selective and may be employed at various steps in the overall synthetic process.

BRIEF SUMMARY OF THE INVENTION

The present invention relates to a process for preparing a compound of the formula

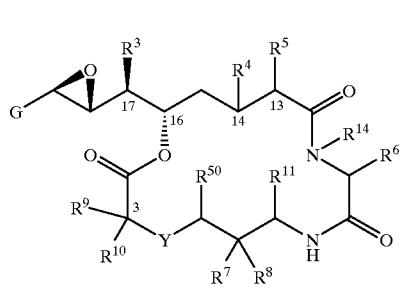

(I)

wherein
G is $C_1-C_{12}$ alkyl, $C_2-C_{12}$ alkenyl, $C_2-C_{12}$ alkynyl, or Ar;
Ar is an aromatic or heteroaromatic group or a substituted aromatic or heteroaromatic group;
$R^3$ is $C_1-C_6$ alkyl;
$R^4$ and $R^5$ are each hydrogen; or $R^4$ and $R^5$ taken together form a second bond between C-13 and C-14;
$R^7$ and $R^8$ are each independently hydrogen or $C_1-C_6$ alkyl; or
$R^7$ and $R^8$ taken together form a cyclopropyl or cyclobutyl ring;
$R^9$ is hydrogen, $C_1-C_6$ alkyl, $C_2-C_6$ alkenyl, $C_2-C_6$ alkynyl, $-(CH_2)_m-(C_3-C_5)$cycloalkyl or benzyl, wherein m is the integer one to three;
$R^{10}$ is hydrogen or $C_1-C_6$ alkyl;
$R^{11}$ is hydrogen, $C_1-C_6$ alkyl, phenyl or benzyl;
$R^{14}$ is hydrogen or $C_1-C_6$ alkyl;
$R^{50}$ is hydrogen or (=O);
Y' is CH, O, NH, SO, $SO_2$ or $(C_1-C_3)$alkylamino;
$R^6$ is $C_1-C_6$ alkyl, substituted $(C_1-C_6)$alkyl, $(C_3-C_8)$ cycloalkyl, substituted $(C_3-C_8)$cycloalkyl, a heteroaromatic or substituted heteroaromatic group or a group of formula (IA), (IB) or (IC):

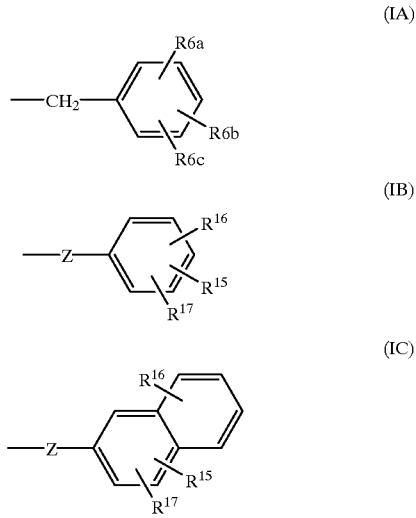

$R^{6a}$, $R^{6b}$, and $R^{6c}$ independently are H, halo or $OR^{18}$;
$R^{15}$, $R^{16}$, and $R^{17}$ independently are hydrogen, halo, $(C_1-C_6)$alkyl, $OR^{18}$, O-aryl, $NH_2$, $NR^{18}R^{19}$, $NO_2$, $OPO_4H_2$, $(C_1-C_6$ alkoxy)phenyl, S-benzyl, $CONH_2$, $CO_2H$, $PO_3H_2$, $SO_2R^{23}$, or Z';
$R^{18}$ and $R^{19}$ independently are hydrogen or $C_1-C_6$ alkyl;
$R^{23}$ is hydrogen or $(C_1-C_3)$alkyl;
Z is $-(CH_2)_n-$ or $(C_3-C_5)$cycloalkyl;
n is 0, 1, or 2; and
Z' is an aromatic or substituted aromatic group; or a pharmaceutically acceptable salt thereof;
comprising epoxidizing a compound of the formula

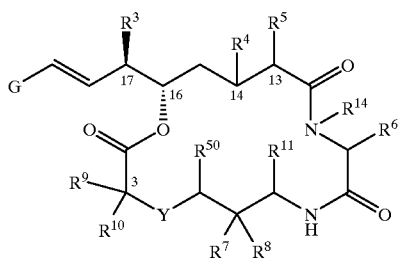

(4)

wherein G, $R^3$, $R^4$, $R^5$, $R^6$, $R^7$, $R^8$, $R^9$, $R^{10}$, $R^{11}$, $R^{14}$ and $R^{50}$ are as defined above and Y is Y' or S; with an oxidant and a chiral ketone to form a compound of formula (I); and optionally forming a pharmaceutically acceptable salt thereof.

This invention further comprises a process for preparing a compound of the formula

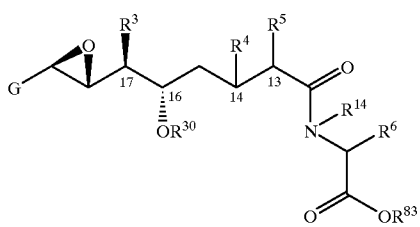

(II)

wherein

G is $C_1$–$C_{12}$ alkyl, $C_2$–$C_{12}$ alkenyl, $C_2$–$C_{12}$ alkynyl, or Ar;

Ar is an aromatic or heteroaromatic group or a substituted aromatic or heteroaromatic group;

$R^3$ is $C_1$–$C_6$ alkyl;

$R^4$ and $R^5$ are each hydrogen; or $R^4$ and $R^5$ taken together form a second bond between C-13 and C-14;

$R^{83}$ is hydrogen, $C_1$–$C_6$ alkyl, trichloroethyl, or —$CH_2SR^{81}$;

$R^{30}$ is hydrogen, an alcohol protecting group, or a group of the formula

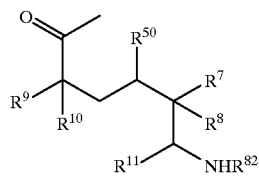

$R^7$ and $R^8$ are each independently hydrogen or $C_1$–$C_6$ alkyl; or $R^7$ and $R^8$ taken together form a cyclopropyl or cyclobutyl ring;

$R^9$ is hydrogen, $C_1$–$C_6$ alkyl, $C_2$–$C_6$ alkenyl, $C_2$–$C_6$ alkynyl, —$(CH_2)_m$—$(C_3$–$C_5)$cycloalkyl or benzyl, wherein m is the integer one to three;

$R^{10}$ is hydrogen or $C_1$–$C_6$ alkyl;

$R^{11}$ is hydrogen, $C_1$–$C_6$ alkyl, phenyl or benzyl;

$R^{14}$ is hydrogen or $C_1$–$C_6$ alkyl;

$R^{50}$ is hydrogen or (=O);

Y is CH, O, $NR^{12}$, S, SO, $SO_2$, wherein $R^{12}$ is H or $C_1$–$C_3$ alkyl;

$R^6$ is $C_1$–$C_6$ alkyl, substituted $(C_1$–$C_6)$alkyl, $(C_3$–$C_8)$ cycloalkyl, substituted $(C_3$–$C_8)$cycloalkyl, a heteroaromatic or substituted heteroaromatic group or a group of formula (IA), (IB) or (IC):

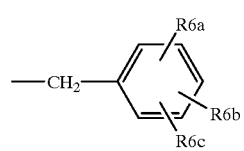

(IA)

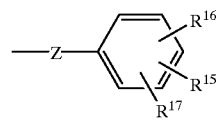

(IB)

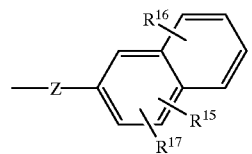

(IC)

$R^{6a}$, $R^{6b}$, and $R^{6c}$ independently are H, $(C_1$–$C_6)$alkyl, halo $NR^{18}R^{19}$ or $OR^{18}$;

$R^{15}$, $R^{16}$, and $R^{17}$ independently are hydrogen, halo, $(C_1$–$C_6)$alkyl, $OR^{18}$, O-aryl, $NH_2$, $NR^{18}R^{19}$, $NO_2$, $OPO_4H_2$, $(C_1$–$C_6$ alkoxy)phenyl, S-benzyl, $CONH_2$, $CO_2H$, $PO_3H_2$, $SO_2R^{23}$, or Z';

$R^{18}$ and $R^{19}$ independently are hydrogen or $C_1$–$C_6$ alkyl;

$R^{23}$ is hydrogen or $(C_1$–$C_3)$alkyl;

Z is —$(CH_2)_n$— or $(C_3$–$C_5)$cycloalkyl;

n is 0, 1, or 2; and

Z' is an aromatic or substituted aromatic group;

$R^{81}$ is $C_1$–$C_6$ alkyl, $C_3$–$C_8$ cycloalkyl, phenyl or benzyl; and $R^{82}$ is a base labile protecting group; or a pharmaceutically acceptable salt thereof; with the proviso that when $R^{83}$ is —$CH_2SR^{81}$, $R^{30}$ is not hydrogen or an alcohol protecting group; with the further proviso that when $R^{83}$ is trichloroethyl, $R^{30}$ is not an alcohol protecting group;

comprising epoxidizing a compound of the formula

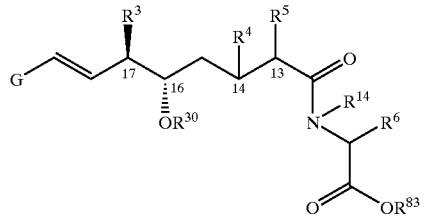

(5)

wherein G, $R^3$, $R^4$, $R^5$, $R^6$, $R^{14}$, $R^{30}$ and $R^{83}$ are as defined above; with an oxidant and a chiral ketone to form a compound of formula (II); and optionally forming a pharmaceutically acceptable salt thereof. The compounds of formula (II) are useful as intermediates in preparing compounds of formula (I).

This invention further comprises the novel compounds of formulae (IId), (18) and (19), disclosed herein, useful in the preparation of compounds of formula (I).

DETAILED DESCRIPTION OF THE INVENTION

As used in the application:

(a) the designation "▶—" refers to a bond that protrudes forward out of the plane of the page;

(b) the designation "⦀⦀⦀⦀" refers to a bond that protrudes backward out of the plane of the page; and (c) the designation "⁓" refers to a bond for which the stereochemistry is not designated.

As used herein, the term "pharmaceutically acceptable salt" refers to either acid addition salts or base addition salts.

The expression "pharmaceutically acceptable acid addition salt" is intended to apply to any non-toxic organic or inorganic acid addition salt of the compounds of formula I or any of its intermediates. Illustrative inorganic acids which form suitable salts include hydrochloric, hydrobromic, sulphuric, and phosphoric acid and acid metal salts such as sodium monohydrogen orthophophate, and potassium hydrogen sulfate. Illustrative organic acids which form suitable salts include the mono-, di- and tricaboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxy-benzoic, and sulfonic acids such as p-toluenesulfonic acid, methane sulfonic acid and 2-hydroxyethane sulfonic acid. Such salts can exist in either hydrated or substantially anhydrous form.

The expression "pharmaceutically acceptable basic addition salts" is intended to apply to any non-toxic organic or inorganic basic addition salts of the compounds of formula I or any of its intermediates. Illustrative bases which form suitable salts include alkali metal or alkaline-earth metal hydroxides such as sodium, potassium, calcium, magnesium or barium hydroxides; ammonia and aliphatic, cyclic or aromatic organic amines such as methylamine, dimethylamine, trimethylamine, diethylamine, triethylamine, isopropyldiethylamine, pyridine and picoline.

As used herein, the term "$C_1$–$C_{12}$ alkyl" refers to a saturated straight or branched chain hydrocarbon group of from one to twelve carbon atoms. Included within the scope of this term are methyl, ethyl, n-propyl, isopropyl, n-butyl, isobutyl, sec-butyl, tert-butyl, pentyl, neopentyl, 2-methylbutyl, 3-methylbutyl, hexyl, heptyl, octyl, nonyl, decyl and the like. Included within the term is the term "$C_1$–$C_6$ alkyl" which refers to a saturated, unsaturated, straight or branched chain hydrocarbon radical of from one to six carbon atoms. Included within the scope of this term are methyl, ethyl, n-propyl, isopropyl, n-butyl, isobutyl, sec-butyl, tert-butyl, pentyl, neopentyl, 2-methylbutyl, 3-methylbutyl, hexyl and the like. Included within the terms "$C_1$–$C_{12}$ alkyl" and "$C_1$–$C_6$ alkyl" is the terms "$C_1$–$C_3$ alkyl" which refers to a saturated, unsaturated, straight or branched chain hydrocarbon radical of from one to three carbon atoms. Included within the scope of this term are methyl, ethyl, isopropyl, and the like.

"Substituted ($C_1$–$C_6$)alkyl" refers to a $C_1$–$C_6$ alkyl group that may include up to three (3) substituents containing one or more heteroatoms. Examples of such substituents are OH, $NH_2$, $CONH_2$, $CO_2H$, $PO_3H_2$ and $SO_2R^{21}$ wherein $R^{21}$ is hydrogen, $C_1$–$C_3$ alkyl or aryl.

The term "($C_3$–$C_8$)cycloalkyl" refers to a saturated $C_3$–$C_8$ cycloalkyl group. Included within this group are cyclopropyl, cyclobutyl, cyclohexyl, cyclooctyl, and the like. A "substituted ($C_3$–$C_8$)cycloalkyl group" refers to a ($C_3$–$C_8$)cycloalkyl group having up to three $C_1$–$C_3$ alkyl, halo, or $OR^{21}$ substituents. The substituents may be attached at any available carbon atom. Cyclohexyl is an especially preferred cycloalkyl group. The term "—$(CH_2)_m$—($C_3$–$C_5$) cycloalkyl" where m is an integer one, two or three refers to a cyclopropyl, cyclobutyl or cyclopentyl ring attached to a methylidene, ethylidene or propylidene substituent.

The term "$C_2$–$C_{12}$ alkenyl" refers to an unsaturated straight or branched chain hydrocarbon radical of from two to twelve carbon atoms and having from one to three double bonds. Included within the scope of this term are ethenyl, propenyl, isopropenyl, n-butenyl, isobutenyl, pentenyl, 2-methylbutenyl, 3-methylbutenyl, hexenyl, octenyl, nonenyl, decenyl and the like. It is especially preferred that alkenyl have only one double bond.

The term "$C_2$–$C_{12}$ alkynyl" refers to an unsaturated straight or branched chain hydrocarbon radical of from two to twelve carbon atoms and having from one to three triple bonds. Included within the scope of this term are ethynyl, propynyl, isopropynyl, 2-methypropynyl, hexynyl, decynyl, and the like. It is particularly preferred that alkynyl has only one triple bond.

The term "$C_1$–$C_6$ alkoxy" refers to a straight or branched alkoxy group containing from one to six carbon atoms, such as methoxy, ethoxy, n-propoxy, isopropoxy, n-butoxy, isobutoxy, pentoxy, 2-methylpentoxy, and the like. The term "($C_1$–$C_6$ alkoxy)phenyl" refers to a phenyl group substituted with a $C_1$–$C_6$ alkoxy group at any available carbon on the phenyl ring.

The term "halo" refers to chloro, bromo, fluoro, or iodo.

The terms "aromatic group" and "heteroaromatic group" refer to common aromatic rings having 4n+2 pi electrons in a monocyclic or bicyclic conjugated system. The term "aryl" refers to an aromatic group, and the term "aralkyl" refers to an aryl($C_1$–$C_6$-alkyl) group. Examples of aromatic groups are phenyl, benzyl and naphthyl. Heteroaromatic groups will contain one or more oxygen, nitrogen and/or sulfur atoms in the ring. Examples of heteroaromatic groups include furyl, pyrrolyl, thienyl, pyridyl and the like. When the aromatic or heteroaromatic groups are substituted, they may have from one to three independently selected $C_1$–$C_6$ alkyl, $C_1$–$C_6$-alkoxy or halo, substituents. The aromatic groups may be further substituted with trifluoromethyl, $COOR^{57}$ (wherein $R^{57}$ is hydrogen or $C_1$–$C_6$ alkyl), $PO_3H$, $SO_3H$, $SO_2R^{57}$, $N(R^{59})(R^{60})$ (wherein $R^{59}$ is hydrogen or $C_1$–$C_6$ alkyl and $R^{60}$ is hydrogen, $C_1$–$C_6$ alkyl, BOC or FMOC), —CN, —$NO_2$, —$OR^{57}$, —$CH_2OC(O)(CH_2)_{m'}NH_2$ (wherein m' is an integer 1 to 6) or —$CH_2$—O—$Si(R^{57})(R^{58})(R^{59})$ (wherein $R^{58}$ is hydrogen or $C_1$–$C_6$ alkyl). Especially preferred substituents for the aromatic groups include methyl, halo, $N(R^{59})(R^{60})$, and —$OR^{57}$. The substituents may be attached at any available carbon atom.

Especially preferred heterocyclic or substituted heterocyclic groups include

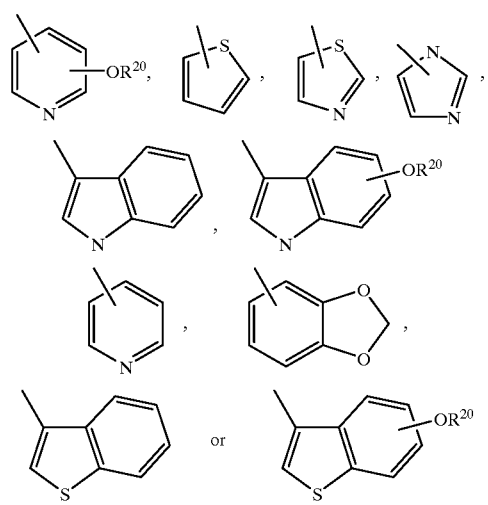

wherein $R^{20}$ is hydrogen or $C_1$–$C_6$ alkyl.

The term "aryl" refers to an aromatic group of from 6 to 12 carbon atoms, such as phenyl or naphthyl groups wherein said groups are optionally substituted with one, two or three substituents selected from the group consisting of $C_1$–$C_4$ alkyl, halo-substituted $C_1$–$C_4$ alkyl, halogen or $C_1$–$C_4$ alkoxy. The terms "lower alkoyl group" or "$C_1$–$C_5$ alkoxy" refers to an alkyloxy radical made up of an oxygen radical bearing a saturated straight or branched chain hydrocarbyl radical of one to five carbon atoms and specifically includes methoxy, ethoxy, propyloxy, isopropyloxy, n-butyloxy, isobutyloxy, sec-butyloxy, tertiary butyloxy, pentyloxy and the like. Specifically included with the scope of the term "aryl" are phenyl, p-toluoyl, p-methoxyphenyl, p-chlorophenyl, naphthyl and the like.

As used herein, the term "heteroaryl" refers to a substituted or unsubstituted heteroaromatic radical which contains one or more non-carbon substituents within the ring, said substituents selected from oxygen, nitrogen or sulfur. The total number of carbon atoms and non-carbon atoms in the ring range from four to twelve atoms. Specifically included with the scope of the term "heteroaryl" are monocyclic conjugated systems such as furyl, pyrrolyl, thienyl, pyridyl, and the like and bicyclic conjugated systems such as indole.

As used herein "epoxide ring" means a three-membered ring whose backbone consists of two carbons and an oxygen atom. As used herein, "aziridine ring" means a three-membered ring whose backbone consists of two carbon atoms and a nitrogen atom. As used herein "sulfide ring" means a three-membered ring whose backbone consists of two carbon atoms and a sulfur atom. As used herein "episulfide ring" means a three-membered ring whose backbone consists of two carbon atoms and a sulfur atom. As used herein "sulfate group" means a five membered ring consisting of a carbon—carbon—oxygen—sulfur—oxygen backbone with two additional oxygen atoms connected to the sulfur atom. As used herein "cyclopropyl ring" means a three member ring whose backbone consists of three carbon atoms. As used herein, "monoalkylphosphate ring" means a five membered ring consisting of a carbon—carbon—oxygen—phosphorous—oxygen backbone with two additional oxygen atoms, one of which bears a lower alkyl group, connected to the phosphorous atom.

As used herein, the term "(=O)" in combination with the carbon on the ring to which it is attached refers to a carbonyl group of the formula

The term "O-aryl" refers to an aryloxy or an aryl group bonded to an oxy moiety.

As used herein, the term "Ph" refers to a phenyl moiety.

As used herein, the term "TBS" refers to tert-butyldimethylsilyl as represented by the formula

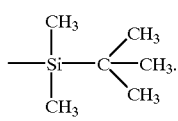

As used herein, the term "NHS" refers to a N-hydroxysuccinimide moiety of the formula

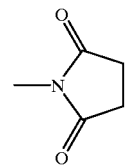

As used herein the term "base labile amino protecting group" refers to common amino protecting groups which are known to be base labile. The artisan can consult common works such as Greene, T. W. "Protecting Groups in Organic Synthesis", Wiley (New York, 1981). See particularly Chapter 7 of Greene. An especially preferred base labile amino protecting group is fluorenylmethoxycarbonyl (Fmoc).

The term "suitable activatable carboxy protecting group" refers to carboxy protecting groups containing activatable ester substituents and are known by one of ordinary skill in the art and disclosed by Greene, T. W., supra. Suitable carboxy protecting groups are those which are activatable ester substituents including N-hydroxy-succinimide, N-hydroxysulfosuccinimide and salts thereof, 2-nitrophenyl, 4-nitrophenyl, 2,4-dichlorophenyl, and the like. An especially preferred activatable carboxy protecting group is N-hydroxy-succinimide (NHS).

As used herein, the term "oxidant" has the meaning associated with the term by the artisan. For example, an oxidant is an agent capable of converting an alkene moiety of a chemical intermediate of this invention to an epoxide moiety. Suitable oxidants include potassium peroxomonosulfate (Oxone), m-CPBA, methyltrioxorhenium (VII), trifluoroper-acetic acid, and magnesium monoperoxyphthalate. A preferred oxidant is potassium peroxomonosulfate (Oxone).

As used herein, the term "chiral ketone" refers to a ketone containing the following general features:

1) the stereogenic centers are close to the reacting center; and
2) the ketone has a fused ring and a a quaternary center α to a carbonyl group; and
3) one face of the ketone is sterically blocked. One especially preferred chiral ketone is of the structure:

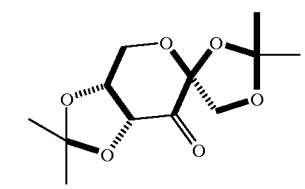

(7)

As used herein the term "alcohol protecting group" can be selected using common works. The term refers to alcohol protecting groups that can be selected from works such as Greene, T. W. "Protecting Groups in Organic Synthesis", Wiley (New York, 1981). See especially Chapter 2 of Greene. Preferred alcohol protecting groups are selected from silyl and acyl groups. An especially preferred group is tert-butyldimethylsilyl (TBS).

A general synthetic procedure for preparing a compound of formula (I) is set forth in Scheme A. In Scheme A, all substituents unless otherwise indicated, are as previously defined. Reagents, techniques, and procedures used in Scheme A are well known and appreciated by one of ordinary skill in the art.

SCHEME A

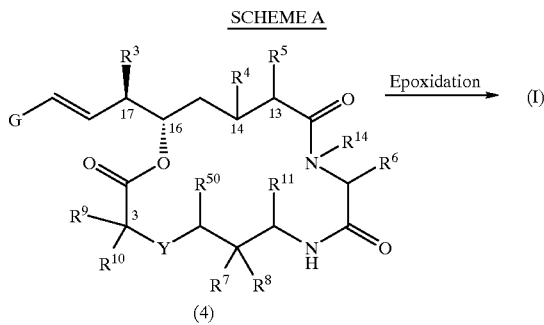

In Scheme A, an alkene of formula (4) is epoxidized with a chiral ketone and an oxidant to form a β-epoxide of formula (I).

For example, a compound of formula (4) may be stereoselectively epoxidized to form a β-epoxide of formula (I) using a chiral ketone with an oxidant in the presence of a suitable base such as $NaHCO_3$ using procedures analogous to those disclosed by Tu, Y. et al, *J. Am. Chem. Soc.* 118, 9806 (1996); Wang, Z-X et al. *J. Org. Chem.* 62, 2328 (1997); Wang, Z-X et al., *J. Am. Chem. Soc.* 119, 11224 (1997). Preferred compounds of formula (4) for this reaction include those compounds where G is phenyl, $R^3$ is methyl, $R^4$ and $R^5$ form a second bond, $R^{14}$ is hydrogen, $R^{11}$ is hydrogen, $R^{50}$ is (=O), and Y is O. The preferred oxidant is Oxone and the preferred chiral ketone is the compound of formula (7).

This preferred chiral ketone can be prepared from D-fructose by ketalization and oxidation under routine conditions. For example, the ketalization can be completed using acetone, $HClO_4$, and the process is conducted at about 0° C. For example, the oxidation can be completed using pyridinium chlorochromate at room temperature. These reactions are known in the art; see, for example: Tu, Y. et al, supra. and Wang, Z-X et al. supra. The asymmetric epoxidation can be carried out at a pH within the range of from about 7.0 to about 11.5.

Although it requires about 3–4 equivalents of chiral ketone to obtain conversions of greater than 95% with many cryptophycin intermediates at a pH of about 8.0, it is possible to use less chiral ketone (about 1–2 equivalents) at a pH of about 9.0 or above. Suitable solvents useful for the epoxidation step include $H_2O$, DMF, glyme, dioxane, $CH_3CN$, alcohols, THF, EtOAc, halohydrocarbons, chlorobenzene, and toluene, with a $CH_3CN/H_2O$ solvent combination being preferred. Reaction temperatures may range from about –20° C. to about 25° C. with about –10° C. to about 10° C. being preferred. The β-epoxide of formula (I), can be isolated and purified by techniques well known in the art such as extraction, evaporation, chromatography and recrystallization. A preferred stereoselective epoxidation utilizes the chiral ketone of structure (7) to provide a mixture of epoxides (α and β) in the crude product (I) in the ratio of about α:β 1:5. This procedure can also be utilized analogously to obtain the α-epoxide derivative of formula (I).

The alkenes of formula (4) are known and may be prepared according to techniques and procedures known in the art. Barrow, R. A. et al. *J. Am. Chem. Soc.* 117, 2479 (1995); PCT Intnl. Publ. No. WO 97/07798, published Mar. 6, 1997, PCT Intnl. Publ. No. WO 96/40184, published Dec. 19, 1996.

A general synthetic procedure for preparing a compound of formula (II), useful as an intermediate for making the β-epoxides of formula (I), is set forth in Scheme B. In Scheme B, $R^{83'}$ is hydrogen or $C_1$–$C_6$ alkyl; $R^{83}$ is a base labile protecting group; $R^{30'}$ is an alcohol protecting group; and q is an integer 1 or 2. All other substituents unless otherwise indicated, are as previously defined. Reagents, techniques, and procedures used in Scheme B are well known and appreciated by one of ordinary skill in the art.

SCHEME B

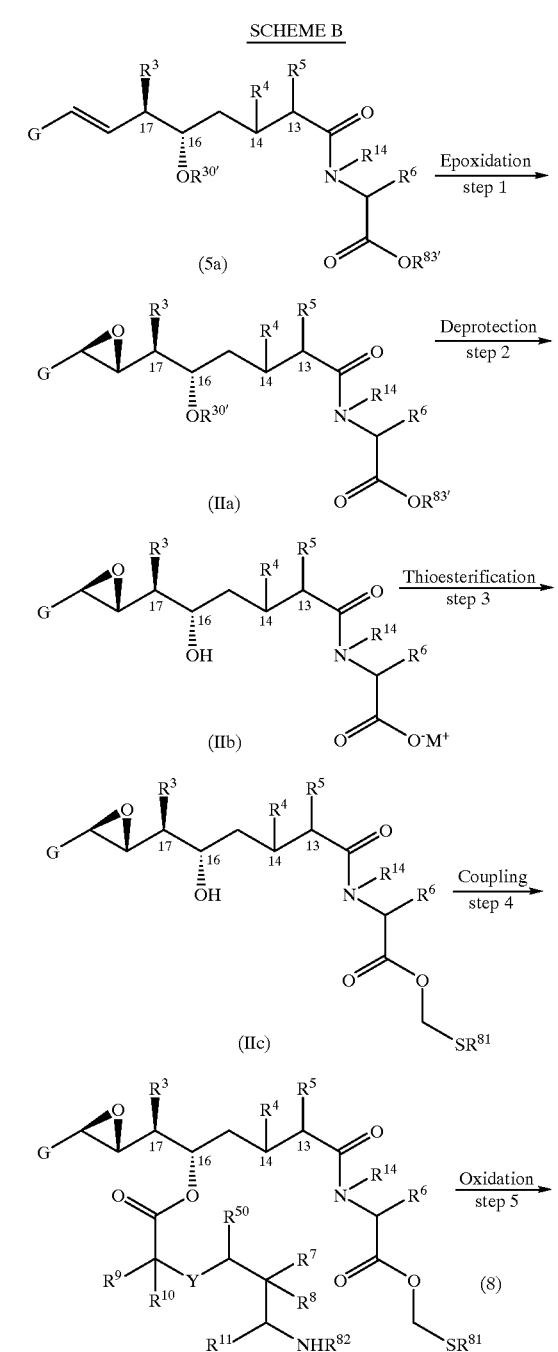

-continued

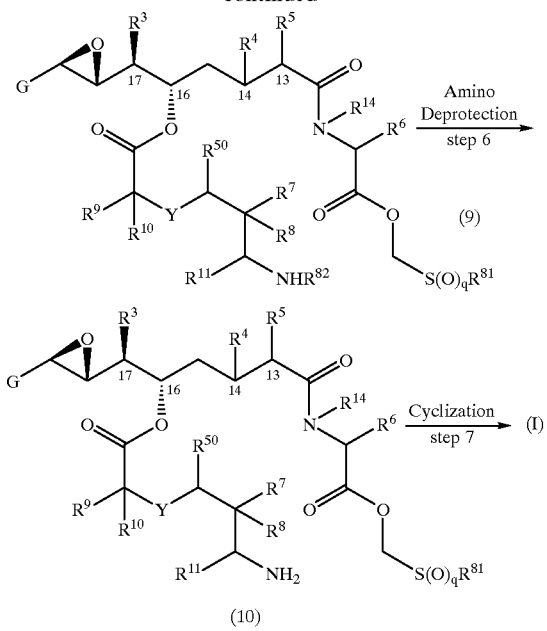

In Scheme B, step 1, an alkene of formula (5a) is epoxidized with a chiral ketone and an oxidant according to the procedure set forth in Scheme A to form a fragment A-B β-epoxide of formula (IIa).

In Scheme B, step 2, a fragment A-B β-epoxide of formula (IIa) is deprotected with a suitable alkoxy deprotecting agent to form a compound of formula (IIb).

A suitable alkoxy deprotecting agent is one that removes the hydroxy protecting group signified by the $R^{30'}$ substituent while inert to the epoxide moiety of the fragment A-B compound of formula (IIa). Preferred deprotecting agents include basic fluoride sources such as tetrabutylammonium fluoride, pyridinium fluoride, triethylammonium fluoride, cesium fluoride, and the like, with tetrabutylammonium fluoride being preferred. The deprotection reaction takes place in the presence of a suitable organic solvent such as tetrahydrofuran, optionally in the presence of a suitable base, such as sodium bicarbonate ($NaHCO_3$). The reaction takes place in the range of from about 0° C. to about 80° C. with from about 20° C. to about 70° C. being preferred. The reaction is run for a period of time ranging from about 3 to 24 hours. Crude product (IIb) may be used without further purification. Alternatively, the compound of formula (IIb) may be isolated and purified according to procedures well known well known in the art such as extraction, evaporation, chromatography and recrystallization.

In Scheme B, step 3, the compound of formula (IIb) is contacted with a thioester forming agent to provide the thioester of formula (IIc).

The term "thioester forming agent" encompasses any suitable means or conditions for forming the thioester moiety of formula (IIc). Included within this definition are the conditions set forth and/or analogously described in Ono, N. et al., *Bull. Chem. Soc. Jpn.* 51 (8), 2401 (1978); Ho, Tse-Lok, *Synth. Comm.* 9(4), 267–270 (1979); Narasaka, K. et al., *J. Am. Chem. Soc.* 106 (10), 2954–2960 (1984); L. G. Wade, Jr. et al., *Tetrahedron Lett.* 731–732 (1978); Mora, N. et al., *Tetrahedron Lett.* 34 (15), 2461–2464 (1993); and Dossena, A. et al. *J. Chem. Soc. Perkin Trans. I*, 2737 (1981).

For example, the compound of formula (IIb) may be treated with a sterically hindered alkyl halide, such as tert-butylbromide, and a solvent of the formula $(R^{81})(Me)SO$, wherein $R^{81}$ is as defined above, in the presence of a suitable base, such as sodium bicarbonate ($NaHCO_3$). A preferred solvent for reaction is dimethylsulfoxide (DMSO). Both the sterically hindered alkyl halide and the suitable base are added in a molar excess of about 7.0 to 12.0 in comparison to the compound of formula (IIb). The reaction takes place in the range of from about 0° C. to about 60° C. with from about 10° C. to about 30° C. being preferred. The reaction is run for a period of time ranging from about 1 to 24 hours. Crude product (IIc) may be used without further purification. Alternatively, the thioester of formula (IIc) may be isolated and purified according to procedures well known well known in the art such as extraction, evaporation, chromatography and recrystallization.

In those instances when the substituent $R^{83'}$ is a moiety other than hydrogen, the compound of formula (IIb) must first be carboxy-deprotected. Carboxy-deprotections under basic conditions are known by those of ordinary skill in the art. For example, the compound of formula (IIb) may be treated with a suitable base, such as lithium hydroxide (LiOH) for a period of time sufficient to remove the carboxy protecting group, for example from about 1 to 24 hours.

In Scheme B, step 4, a β-epoxy thioester of formula (IIc) is coupled with a carboxylic acid of the formula

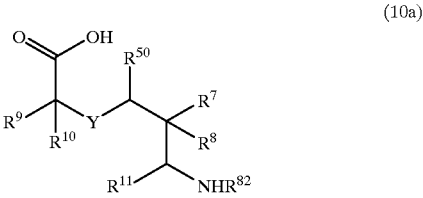

wherein $R^7$, $R^8$, $R^9$, $R^{10}$, $R^{11}$, $R^{50}$ and $R^{82}$ are as defined above to provide the compound of formula (8).

For example, the carboxylic acid of formula (10a) is dissolved in a suitable organic solvent, such as DMF, glyme, dioxane, THF, $CH_3CN$, EtOAc, and halohydrocarbons, with dichloromethane being preferred. This solution is then treated with a coupling reagent. Possible coupling reagents include DCC, EDCI, and similar reagents, such as DMAP which activate carboxylic acids towards esterification with alcohols. This solution may then be optionally treated with a suitable base such as solid sodium bicarbonate and then contacted with a β-epoxy thioester of formula (IIc). The concentration of (10a) after these additions should range from about 0.1 M to about 2.0 M. The reaction takes place in the range of from about –30° C. to about 60° C. with from about 10° C. to about 30° C. being preferred. The reaction is run for a period of time ranging from about 0.5 to 12 hours. Crude product (8) may be used without further purification. Alternatively, the compound of formula (8) may be isolated and purified according to procedures well known well known in the art such as extraction, evaporation, chromatography and recrystallization.

In Scheme B, step 5, a β-epoxy thioester of formula (8) is oxidized with a suitable oxidizing agent to provide the sulfone or sulfoxide of formula (9).

A suitable oxidizing agent is an agent capable of converting the sulfide of formula (8) into the sulfone or sulfoxide of formula (9), while inert to the epoxide moiety of the molecule. Suitable oxidizing agents include potassium peroxomonosulfate (Oxone), m-CPBA, methyltrioxorhenium (VII), and magnesium monoperoxyphthalate, with Oxone being preferred.

For example, the sulfide of formula (8) is treated with a suitable base, such as sodium bicarbonate followed by a suitable oxidizing agent, such as Oxone. The reaction is carried out in a suitable solvent, such as acetone, DMF, glyme, dioxane, $CH_3CN$, alcohols, THF, EtOAc, halohydrocarbons, chlorobenzene, and toluene, with acetone being preferred. Generally, the reaction is carried out at temperatures of from about −30° C. to about 50° C. with from about −10° C. to about 10° C. being preferred. Generally, the reaction requires from about 15 minutes to about 5 hours. Crude sulfone or sulfoxide (9) may be used without further purification. Alternatively, the sulfone or sulfoxide of formula (9) may be isolated and purified according to procedures well known well known in the art such as extraction, evaporation, chromatography and recrystallization.

In Scheme B, step 6, the sulfone or sulfoxide of formula (9) is deprotected with a suitable deprotecting agent to provide the amine of formula (10).

A suitable deprotecting agent is an agent capable of removing the base labile substituent $R^{82}$ on the compound of formula (9) while inert to the epoxide moiety of the molecule. Suitable deprotecting agents include bases such as secondary and tertiary amines and inorganic bases, for example, piperidine; morpholine, dicyclohexylamine, p-dimethylaminopyridine, diisopropylethylamine, and the like, with piperidine being preferred. The reaction is carried out in a suitable solvent such as DMF, glyme, dioxane, $CH_3CN$, alcohols, THF, EtOAc, halohydrocarbons, chlorobenzene, or toluene. Generally, the reaction is carried out at a temperature ranging from about 0° C. to about 120° C. Generally, the reaction requires from about 1 to 72 hours. The compound of formula (I) may be isolated and purified by techniques well known in the art, such as extraction, evaporation, chromatography and recrystallization. Alternatively, the compound of formula (10) is isolated and may be further cyclized with a cyclizing agent to provide a compound of formula (I).

Typically, once the compound of formula (9) is deprotected, it undergoes spontaneous cyclization. However, some particular compounds of formula (9) may require an additional cyclization step. For example, the sulfide of formula (8), although much less active than its oxidized counterpart, upon removal of the base-labile protecting group may be cyclized with a suitable cyclizing agent, such as 2-hydroxypyridine to form a compound of formula (I). For example, the sulfide of formula (8), or alternatively a selected compound of formula (10), is heated in a suitable solvent, such as DMF at about 60° C. for several days in the presence of piperidine and 2-hydroxypyridine. The compound of formula (I) is isolated and purified by techniques well known in the art, such as extraction, evaporation, chromatography and recrystallization.

Alternatively, a compound of formula (9) may be formed according to SCHEME B1. In SCHEME B1, all substituents are as previously defined except where otherwise indicated.

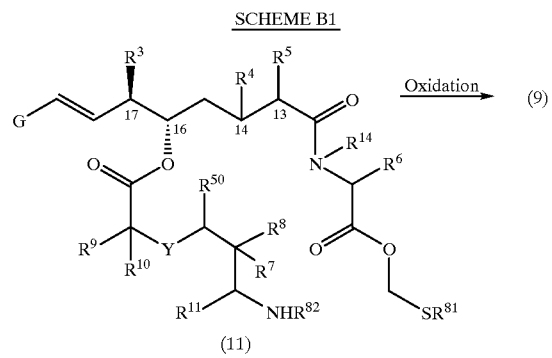

SCHEME B1

In SCHEME B1, alkene of formula (11) is epoxidized with a chiral ketone and an oxidant according to the procedure set forth in Scheme A to form a compound of formula (9). The alkene of formula (11) may be prepared by one of ordinary skill in the art according to analogously known techninques and procedures. During the epoxidation reaction, the sulfide moiety of compound (11) is oxidized to form the sulfoxide or sulfone moiety of compound (9).

Optionally, on those compounds of formula (I) containing basic or acidic functional groups, pharmaceutically acceptable salts of the compounds of formula (I) may be formed using standard techniques. For example, the free base may be dissolved in aqueous or aqueous-alcohol solution or other suitable solvent containing the appropriate acid and the salt isolated by evaporating the solution. Alternatively, the free base may be reacted in an organic solvent containing the appropriate acid and the salt isolated by evaporating the solution. Further, the free base may be reacted in an organic solvent in which case the salt separates directly or can be obtained by concentration of the solution or in a solvent such as water which is then removed in vacuo or by freeze-drying, or by exchanging the cations of an existing salt for another cation on a suitable ion exchange resin.

A synthetic scheme for making the carboxylic acids of formula (10a) is set forth in Scheme C. The reagents and starting material are readily available to one of ordinary skill in the art. In Scheme C, all substituents, unless otherwise indicated, are as previously defined.

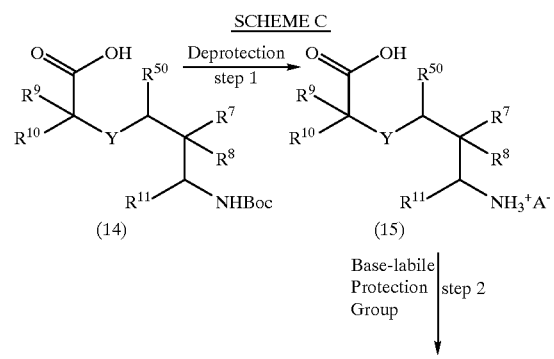

SCHEME C

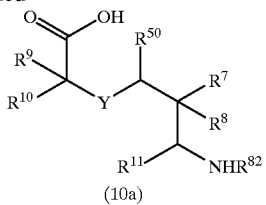

(10a)

In Scheme C, step 1, the Boc-protected amine of formula (14) is deprotected to provide the deprotected amine of formula (15).

For example, the deprotection reaction involves the removal of an amino protecting group by techniques and procedures well known and appreciated by one of ordinary skill in the art. The selection, use, and removal of protecting groups are set forth by Greene, T. W. "Protecting Groups in Organic Synthesis", Wiley (New York, 1981). For example, the Boc-protected amine of formula (14) is dissolved in a suitable acid, such as trifluoroacetic acid or hyrdrochloric acid. Generally, the reaction is carried out at a temperature ranging from about 0° C. to about 60° C. Generally, the reaction requires from about 1 to 24 hours. The deprotected amine of formula (15) may be isolated and purified by techniques well known in the art, such as extraction, evaporation, chromatography and recrystallization.

The Boc-protected amine of formula (14) is described in Barrow, R. A. et al. *J. Am. Chem. Soc.* 117, 2479 (1995); PCT Intnl. Publ. No. WO 96/40184, published Dec. 19, 1996; and PCT Intnl. Publ. No. WO 97/07798, published Mar. 6, 1997.

In Scheme C, step 2, the deprotected amine of formula (15) is amino-protected with a base-labile amino protecting group to provide the carboxylic acid of formula (10a).

For example, the protection of an amino group with a base-labile amino protecting group involves the addition of a base-labile amino protecting group by techniques and procedures well known and appreciated by one of ordinary skill in the art. The selection, use, and removal of base-labile amino protecting groups are set forth by Greene, T. W. "Protecting Groups in Organic Synthesis", Wiley (New York, 1981). A preferred base-labile amino protecting group is Fmoc. For example, to a solution of the deprotected amine of formula (15) in a suitable solvent, such as dioxane, is added a suitable base, such as sodium bicarbonate, followed by a compound of the formula $R^{82}$-Cl or $R^{82}$-NHS, such as Fmoc-Cl or Fmoc-NHS succinimide. The mixture may be optionally diluted with a small amount of water and stirred for a period of time ranging from 12 to 48 hours at a temperature ranging from about 0° C. to about 60° C. The mixture may be quenched with a suitable acid, such as hydrochloric acid. The carboxylic acid of formula (10a) may be isolated and purified by techniques well known in the art, such as extraction, evaporation, chromatography and recrystallization.

A synthetic scheme for making a compound of formula (II) wherein $R^{83}$ is trichloroethyl is set forth in Scheme D. The reagents and starting material are readily available to one of ordinary skill in the art. In Scheme D, all other substituents, unless otherwise indicated, are as previously defined.

SCHEME D

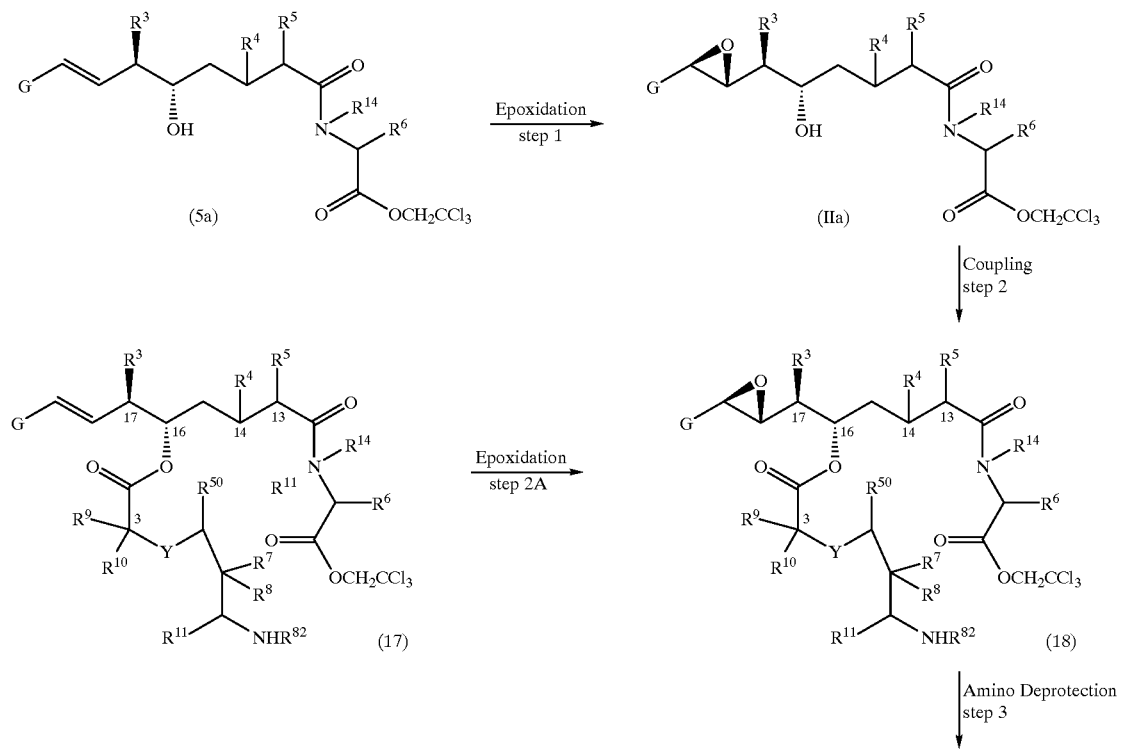

(I) $\xrightarrow{\text{Cyclization step 4}}$

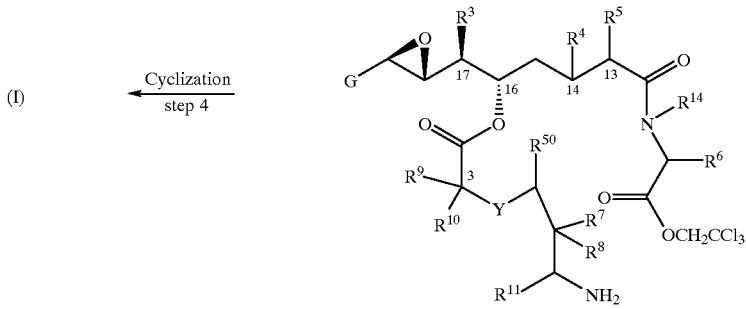

In Scheme D, step 1, the alkene of formula (16) is epoxidized with a chiral ketone and an oxidant according to the procedure set forth in Scheme A to form a β-epoxy compound of formula (IId).

In Scheme D, step 2, a β-epoxy compound of formula (IId) is coupled with a carboxylic acid of formula (10a) according to the procedures described in Scheme B, step 4, to form a compound of formula (18).

In Scheme D, step 2A, an alkene of formula (17) is epoxidized with a chiral ketone and an oxidant according to the procedure set forth in Scheme A to form a compound of formula (18).

In Scheme D, step 3, the compound of formula (18) is base-deprotected with a suitable base-deprotecting agent to provide the compound of formula (19).

A suitable base-deprotecting agent is an agent that is capable of removing the base labile substituent $R^{82}$ on the compound of formula (18) while inert to the epoxide moiety of the molecule. Suitable base-deprotecting agents include bases such as secondary and tertiary amines and inorganic bases, for example, piperidine, morpholine, dicyclohexylamine, p-dimethylaminopyridine, diisopropylethylamine, and the like, with piperidine being preferred. These agents are set forth in Greene, T. W. "Protecting Groups in Organic Synthesis", Wiley (New York, 1981). The reaction is carried out in a suitable solvent such as DMF, glyme, dioxane, $CH_3CN$, alcohols, THF, EtOAc, halohydrocarbons, chlorobenzene, or toluene. Generally, the reaction is carried out at a temperature ranging from about 0° C. to about 120° C. Generally, the reaction requires from about 1 to 72 hours. The compound of formula (19) may be isolated and purified by techniques well known in the art, such as extraction, evaporation, chromatography and recrystallization.

Typically, once the compound of formula (18) is deprotected, it undergoes spontaneous cyclization to provide a compound of formula (I). However, some particular compounds of formula (18) may yield a compound of formula (19) after deprotection and require an additional ring-closing step as set forth in Scheme D, step 4.

In Scheme D, step 4, the compound of formula (19) is cyclized using a ring-closing agent to provide a compound of formula (I).

The ring-closing reaction may be carried out by intramolecular aminolysis. For example, the compound of formula (19) is treated with a suitable cyclizing agent such as 2-hydroxypyridine analogous to the deprotection and cyclization conditions described in Scheme B, steps 6 and 7 to provide a compound of formula (I).

The pharmaceutically acceptable salts of a compound of formula (I), prepared as described in Scheme D, may optionally be formed according to the procedures described in Scheme B.

Some preferred characteristics of this invention are set forth in the following tabular form wherein the features may be independently selected to provide preferred embodiments of this invention. The invention is in no way limited to the features described below:

A) $R^8$ is ethyl, propyl, isopropyl, butyl, isobutyl or isopentyl;

B) $R^7$ is ethyl, propyl, isopropyl, butyl, isobutyl, pentyl, or isopentyl;

C) $R^7$ is H, $R^8$ is methyl, $R^3$ is methyl, and X and Y are not both O;

D) $R^3$ is ethyl, propyl, isopropyl, butyl, isobutyl, pentyl or isopentyl;

E) $R^9$ is methyl, ethyl, propyl, butyl, isobutyl, pentyl, or isopentyl;

F) $R^{10}$ is methyl, ethyl, propyl, butyl, isobutyl, pentyl, or isopentyl;

G) Ar is phenyl optionally substituted with a substituent selected from the group consisting of hydrogen, halogen, and simple alkyl;

H) a compound wherein Y is selected from the group consisting of O, NH, S, SO and $SO_2$;

I) a compound wherein Y is C, $R^7$, $R^8$, $R^9$, and $R^{10}$ are each hydrogen; and $R^1$ and $R^2$ form an epoxide;

J) $R^7$, $R^8$ are each hydrogen;

K) $R^7$ and $R^8$ are each selected from hydrogen or OH;

L) Y is NH;

M) R is selected from the group consisting of methyl, ethyl, n-propyl, and phenyl;

N) X is O and Y is NH;

O) $R^4$ and $R^5$ form a double bond;

P) $R^6$ is substituted benzyl wherein one substituent is a halogen and one is an $OR^{12}$ group wherein $R^{12}$ is lower alkyl;

Q) the oxidant is Oxone;

R) the process is utilized to prepare a cryptophycin compound;

S) the epoxidation is selective;

T) the ketone is of the formula:

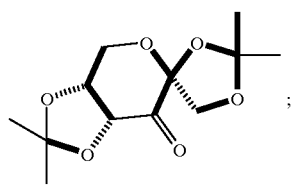

U) $R^p$ is NHS; and

V) $R^7$ and $R^8$ are each methyl.

To provide further guidance for the artisan, the following schemes are provided:

As used in Scheme I' and throughout the specification, $R^{1'}$ is halogen, SH, amino, monoalkylamino, dialkylamino, trialkylammonium, alkylthio, dialkylsulfonium, sulfate, phosphate or a protected OH or protected SH group; $R^2$ is OH or SH; $R^{26}$ is an alcohol protecting group introduced during a portion of the synthetic process to protect an alcohol group which might otherwise react in the course of chemical manipulations, and is then removed at a later stage of the synthesis. Numerous reactions for the formation and removal of such a protecting groups are described in a number of standard works, including, for example, "Protective Groups in Organic Chemistry", Plenum Press, (London and New York, 1973); Greene, T. W. "Protecting Groups in Organic Synthesis", Wiley (New York, 1981). The skilled artisan can select an appropriate alcohol protecting group particularly with guidance provided from such works. One particularly useful alcohol protecting group is tert-butyldimethylsilyl (TBS).

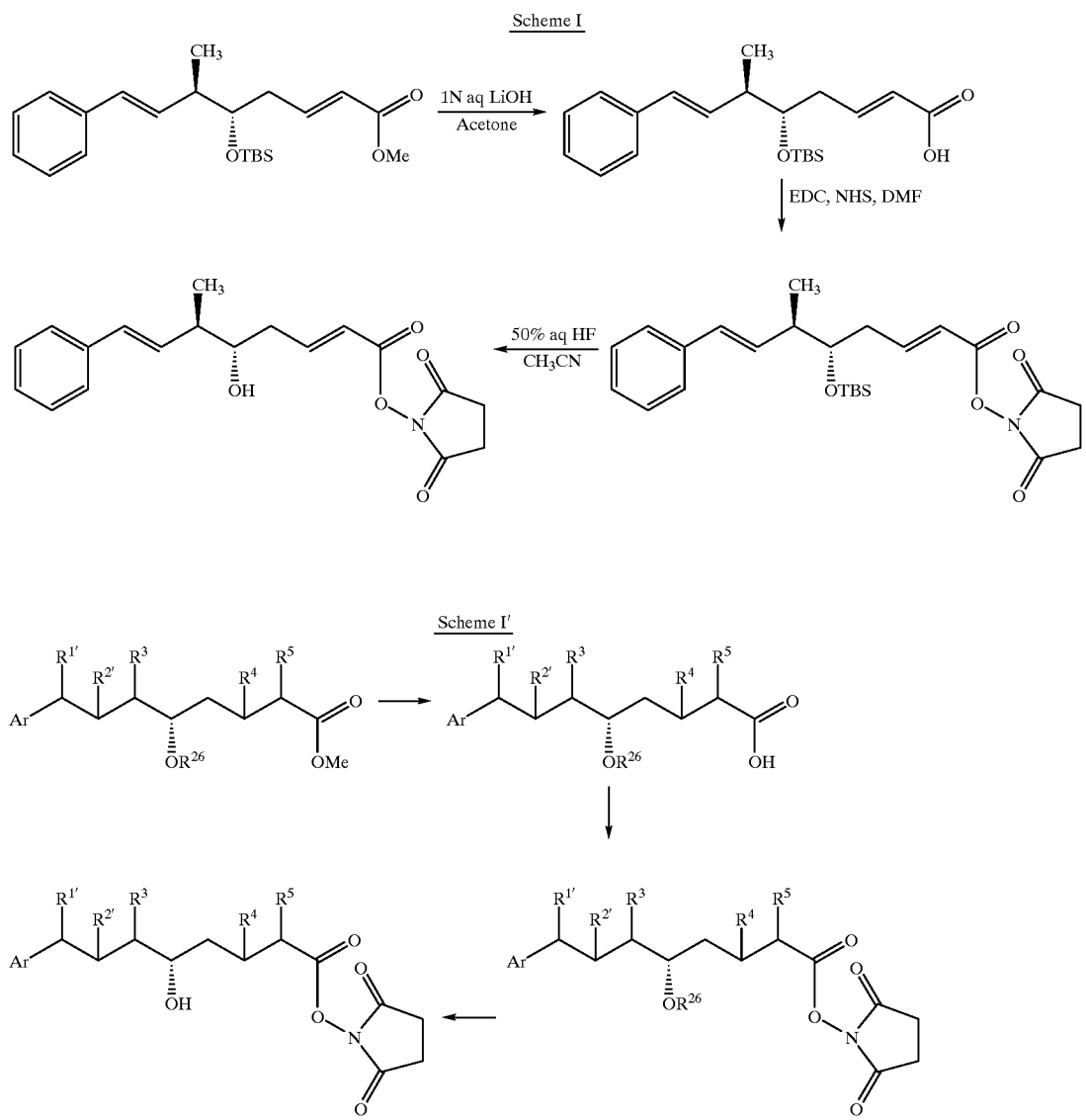

Scheme 2

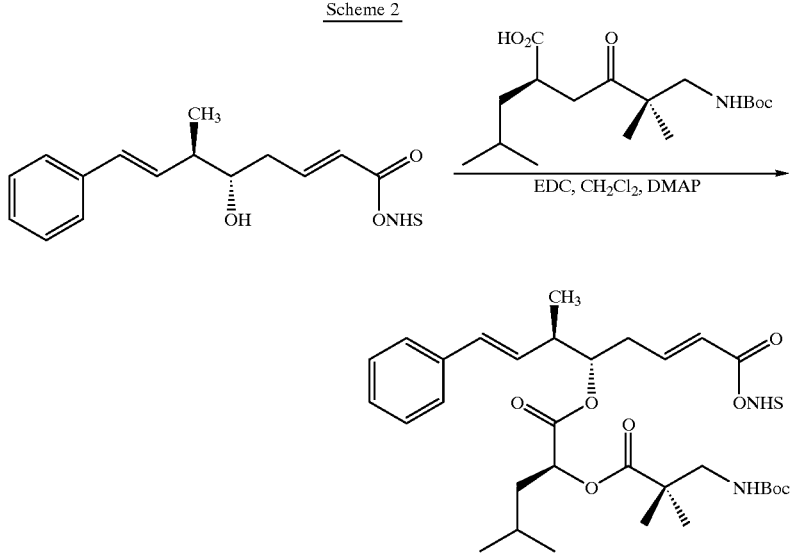

Scheme 3

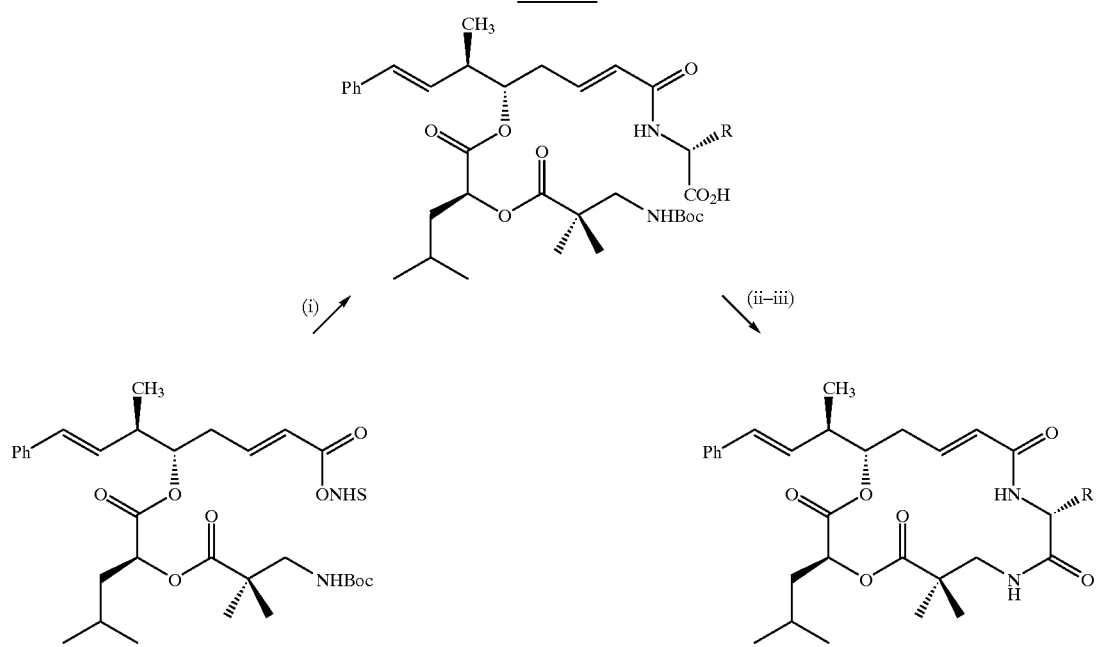

As used in Scheme I' and throughout the specification, $R^{1'}$ is halogen, SH, amino, monoalkylamino, dialkylamino, trialkylammonium, alkylthio, dialkylsulfonium, sulfate, or phosphate; $R^2$ is OH or SH; $R^{26}$ is an alcohol protecting group introduced during a portion of the synthetic process to protect an alcohol group which might otherwise react in the course of chemical manipulations, and is then removed at a later stage of the synthesis. Numerous reactions for the formation and removal of such a protecting group are described in a number of standard works, including, for example, "Protective Groups in Organic Chemistry", Plenum Press, (London and New York, 1973); Greene, T. W. "Protecting Groups in Organic Synthesis", Wiley (New York, 1981). The skilled artisan can select an appropriate alcohol protecting group particularly with guidance provided from such works. One particularly useful alcohol protecting group is tert-butyldimethylsilyl (TBS). The products of such schemes can be derivatized using standard methods to provide other cryptophycin compounds.

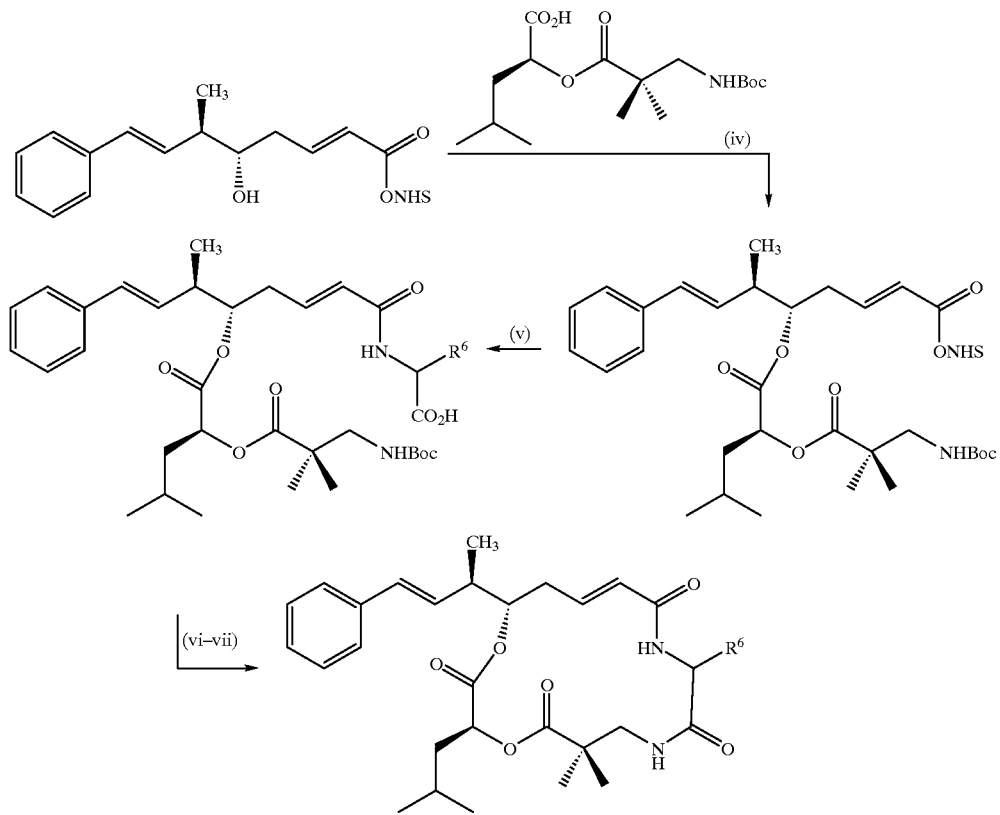
$R^6$ has the meaning defined supra.
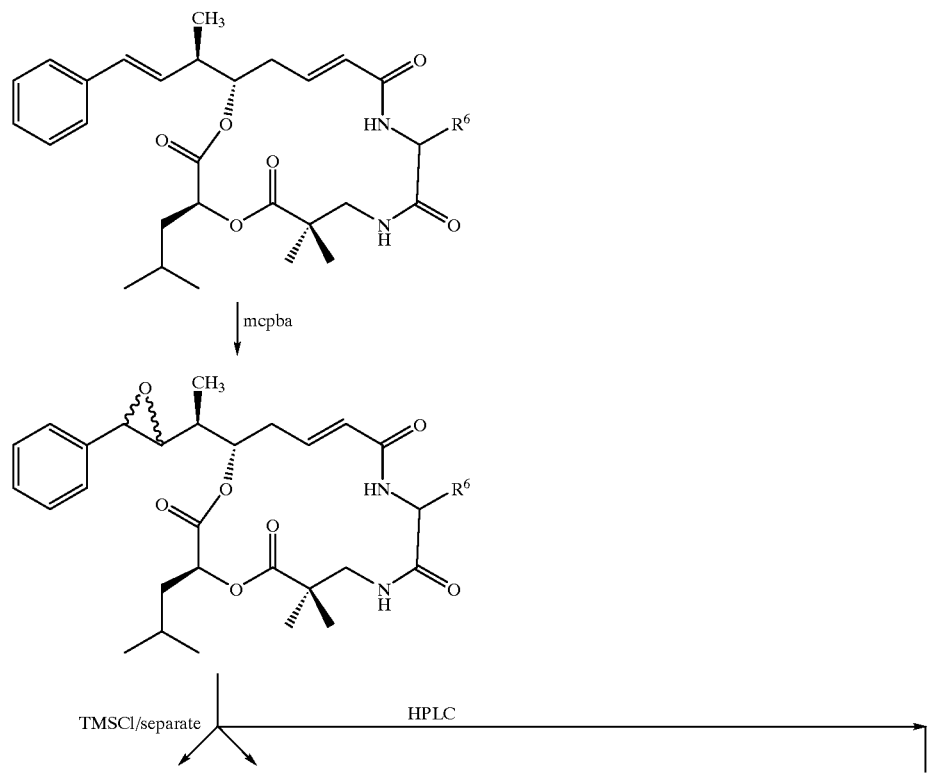

25

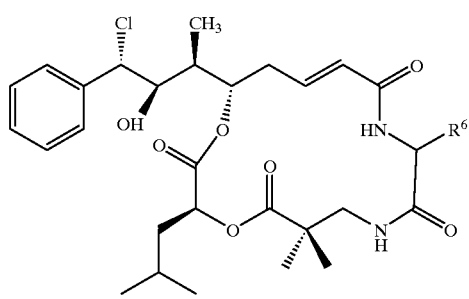

26

-continued

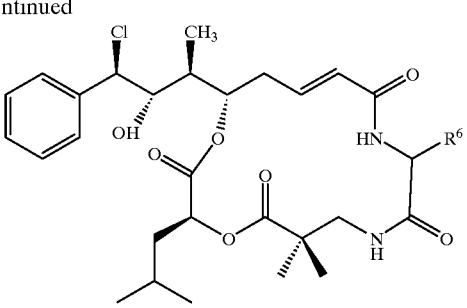

|base

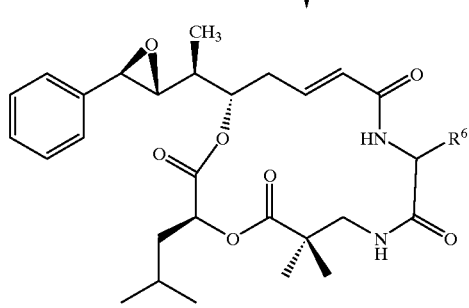

|base

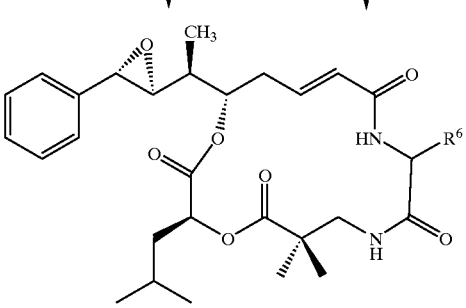

The product of the schemes provided herein can be further derivatized using standard methods to provide further cryptophycin compounds.

The artisan can utilize appropriate starting materials and reagents to prepare desired compounds using the guidance of the previous schemes and following examples.

The ester starting material can be prepared, for example, as follows:

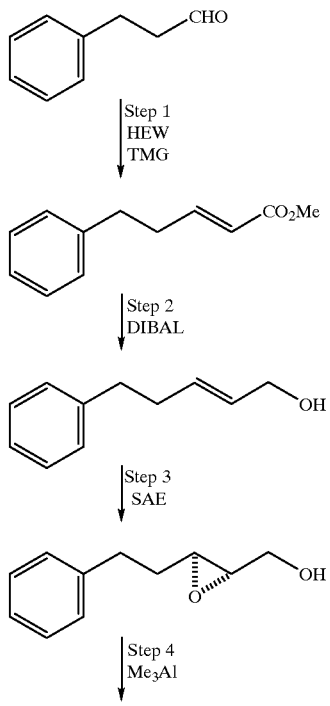

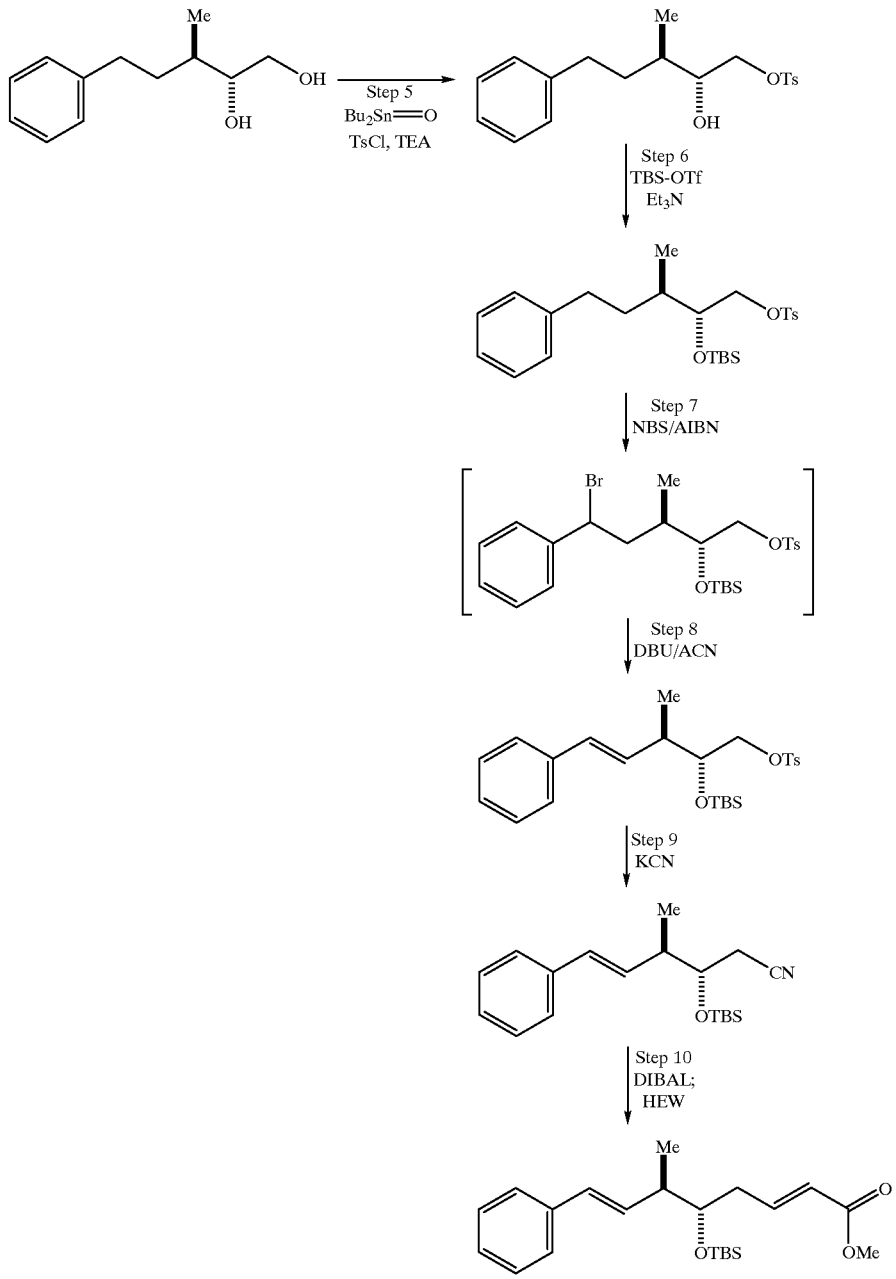

$R^6$ has the meaning defined supra.

The scheme for preparing the ester is further explained by the Preparation Section herein which provides one specific application of the scheme for the convenience of the skilled artisan.

The Scheme for preparing the ester is applicable to the Ar substituents claimed herein. The scheme illustration is not intended to limited the synthesis scheme only to the phenyl ring illustrated. Rather, the artisan can broadly apply this process to provide desired starting materials for the compounds claimed herein.

The scheme for preparing the ester is further explained by the Preparation Section herein which provides one specific application of the scheme for the convenience of the skilled artisan.

Scheme E for preparing the ester is applicable to the Ar substituents claimed herein. The scheme illustration is not intended to limited the synthesis scheme only to the phenyl ring illustrated. Rather, the artisan can broadly apply this process to provide desired starting materials for use in the processes claimed herein.

The necessary reaction time is related to the starting materials and operating temperature. The optimum reaction time for a given process is, as always, a compromise which is determined by considering the competing goals of throughput, which is favored by short reaction times, and maximum yield, which is favored by long reaction times.

To further illustrate the invention the following examples are provided. The scope of the invention is in no way to be construed as limited to or by the following examples.

Preparation 1

Step 1. Methyl 5-Phenylpent-2(E)-enoate

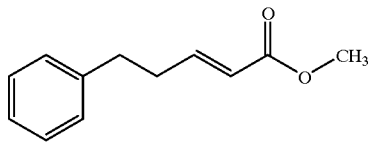

A solution of trimethyl phosphonoacetate (376 g, 417 mL, 2.07 mol) in THF (750 mL) was stirred at 0° C. in a 3 L 3-neck round bottom flask equipped with a mechanical stirrer and $N_2$ inlet. To the chilled solution, neat tetramethyl guanidine (239 g, 260 mL, 2.07 mol) was added dropwise via an addition funnel. The chilled clear pale yellow solution was stirred for 25 minutes at 0° C. A solution of hydrocinnamaldehyde (90%, 253 g, 248 mL, 1.9 mol) in THF (125 mL) was added dropwise to the reaction solution slowly. Upon completion of addition, the reaction was stirred for 10 h rising to room temperature. GC indicated a 95:5 ratio of product to starting material. 500 ml of water was added to the reaction vessel and the reaction stirred overnight separating into two layers. The organic layer was isolated and the aqueous layer was extracted with t-BuOMe. The organic layers were combined and dried over $MgSO_4$, then concentrated in vacuo to yield an orange oil. The crude product was distilled at 129° C./0.3 mm Hg yielding 360.5 g, 91.7% yield, of a clear slightly yellow oil.

EIMS m/z 190(13; M+), 159(410, 158(39), 131(90), 130(62), 117(22), 104(12), 95(57), 91(100), 77(21), 65(59); HREIMS m/z 190.0998 ($C_{12}H_{14}O_2$ D −0.4 mnu); UV lmax (e) 210 (8400), 260 (230) nm; IR nmax 3027, 2949, 1723, 1658, 1454, 1319, 1203, 978, 700 cm$^{-1}$; $^1$H NMR d (CDCl$_3$) 7.15–7.3 (Ph-H5;bm), 7.00 (3-H;dt, 15.6/6.6), 5.84 (2-H;dt, 15.6/1.2), 3.70 (OMe;s), 2.76 (5-H2;t, 7.2), 2.51 (4-H2; bdt, 6.6/7.2); $^{13}$C NMR d (CDCl$_3$) 166.9 (1), 148.3(3), 140.6 (Ph-1'), 128.4/128.2 (Ph2'/3'/5'6'), 126.1 (Ph 4'), 121.4 (2), 51.3 (OMe), 34.2/33.8 (4/5).

Step 2. 5-phenyl-pent-2-en-1-ol

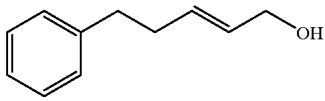

To a 12 L 4-neck round bottom flask equipped with a thermocouple, mechanical stirrer and $N_2$ inlet, a solution of enoate ester (310.5 g, 1.5 mol) in THF (1.5 L) was charged and chilled to −71° C. via a i-PrOH/CO$_2$ bath. To the reaction vessel, was added dropwise DIBAL (2.5 L, 1.5 M in toluene, 3.75 mol) at a rate to maintain the reaction temperature <−50° C. Upon complete addition, the reaction was stirred overnight with the reaction temperature <−50° C. TLC (3:1 Hexanes:EtOAc, SiO$_2$) indicated absence of starting material after 16 h. The reaction temperature was allowed to raise to −15° C. The reaction was quenched slowly with 1N HCl (150 mL). At this point the reaction setup into a gelatinous solid. A spatula was employed to breakup the the semi-solid and 1N HCl (200 mL) was added making the mixture more fluid. Concentrated HCl (625 mL) was charged to form a two phase system. The layers were separated and the product extracted with t-BuOMe. The organic layer was dried over $MgSO_4$ and concentrated in vacuo to yield a clear pale yellow oil, 247.8 g. The crude product was distilled at 145° C./0.25 mm Hg yielding 209.7 g, 86.2%.

EIMS m/z 162 (1:M+) 144 (16), 129 (7), 117 (9) 108 (6), 92 (17), 91 (100), 75 (5), 65 (12), HREIMS m/z 162, 1049 ($C_{11}H_{14}O$, D −0.4 mmu); UV lmax (e) 206 (9900), 260 (360); IR nmax 3356, 2924, 1603, 1496, 1454, 970, 746, 700 cm$^{-1}$; $^1$H NMR d 7.15–7.3 (Ph-H5;m), 5.70 (3-H;dt, 15.6/6.0), 5.61 (2-H;dt, 15.6/4.8), 4.02 (1-H2;d 4.8), 2.68 (5-H2; t, 7.2), 2.40 (OH;bs), 2.36(4-H2; dt, 6.0/7.2); $^{13}$C NMR d141.6 (Ph 1'), 131.8(3), 129.5 (2), 128.3/128.2 (Ph 2'/3'/5'/6'), 125.7 (Ph 4'), 63.3 (1), 35.4/33.8 (4/5).

Step 3. (2S,3S)-2,3-Epoxy-5-phenyl-1-pentanol

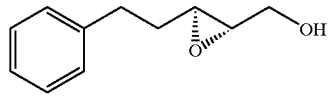

To a 1 L 3 neck round bottom flask equipped with a mechanical stirrer, thermocouple and nitrogen inlet was added CH$_2$Cl$_2$ (350 mL), dried 4 Å molecular sieves (30 g) and L-(+)-diethyl tartrate (7.62 g, 0.037 mol). The resulting mixture was cooled to −20° C. and treated with Ti(O-i-Pr)$_4$ (9.2 mL, 0.031 mol), followed by the addition of t-butylhydroperoxide (4.0 M in CH$_2$Cl$_2$, 182 mL, 0.78 mol) at a rate to maintain the temperature$^2$ −20° C. Upon complete addition, the reaction mixture was stirred for another 30 min, and then treated with a solution of the allylic alcohol (50 g, 0.31 mol) in CH$_2$Cl$_2$ (30 mL) at a rate to maintain the temperature$^2$ −20° C. The reaction was stirred at the same temperature for 5 h, then filtered into a solution of ferrous sulfate heptahydrate (132 g) and tartaric acid (40 g) in water (400 mL) at 0° C. The mixture was stirred for 20 min, then transferred to a separatory funnel and extracted with t-BuOMe (2×200 mL). The combined organic phase was stirred with 30% NaOH solution containing NaCl, for 1 h at 0° C. The layers were again separated, and the aqueous phase extracted with t-BuOMe. The combined organic phase was washed with brine, dried over MgSO$_4$ and concentrated to yield 52.8 g as an amber oil.

Step 4. (2R, 3R)-2-hydroxy-3-methyl-5-phenylpentan-1-ol

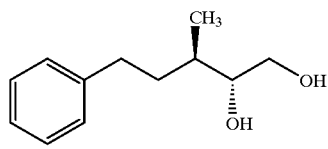

To a 5 L 3 neck round bottom flask equipped with a mechanical stirrer, thermocouple and nitrogen inlet was added hexanes (1 L) and cooled to 0° C. A 2.0M solution of Me$_3$Al in hexanes (800 mL, 1.6 mol) was added, followed by a solution of the epoxide (120 g, 0.677 mol) in hexanes (250 mL)/CH$_2$Cl$_2$ (50 mL) maintaining the temperature below 20° C. Upon complete addition, the cloudy reaction mixture was stirred at 5° C. for 35 min, whereupon a solution of 10% HCl (300 mL) was added dropwise, followed by the addition of concd HCl (350 mL). The layers were separated, and the organic phase was washed with brine and dried over MgSO$_4$. After removal of the volatiles in vacuo, 122.1 gram of an oil was obtained.

Step 5. (2R, 3R)-2-hydroxy-3-methyl-5-phenylpent-1-yl Tosylate

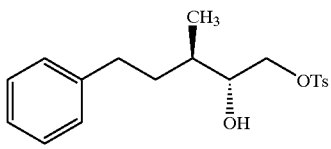

To a 2 L 3 neck round bottom flask equipped with a mechanical stirrer and nitrogen inlet was added the diol (58 g, 0.30 mol), dibutyltin oxide (1.5 g, 0.006 mol, 2 mol %), toluenesulfonyl chloride (57.5 g, 0.30 mol), $CH_2Cl_2$ (580 mL) and triethylamine (42.0 mL, 0.30 mol). The resulting mixture was stirred at room temperature for 2 h (although the reaction was complete within 1 h), filtered, washed with water and dried over $MgSO_4$. Concentration of the volatiles in vacuo afforded 104.1 gram of a slightly amber oil.

Step 6. (2R, 3R)-2-[(tert-Butyldimethylsilyl)oxy]-3-methyl-5-phenylpent-1-yl Tosylate

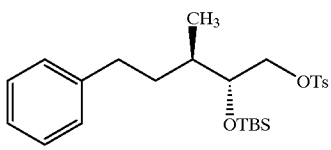

A solution of the tosylate (100 g, 0.29 mol) and triethylamine (81.0 mL, 0.58 mol) in $CH_2Cl_2$ (1200 mL) was treated with neat TBS-OTf (99 mL, 0.43 mol) dropwise with continued stirring for another 20 min. The reaction was washed twice with brine, dried over $MgSO_4$ and concentrated to dryness. The oil was dissolved in a minimal amount of hexanes and filtered over a silica pad, eluting with hexanes:EtOAc (9:1) to yield a slightly amber oil, 134 g.

Step 7. (2R, 3R,5RS)-2-[(tert-Butyldimethylsilyl)oxy]-3-methyl-5-bromo-5-phenylpent-1-yl Tosylate

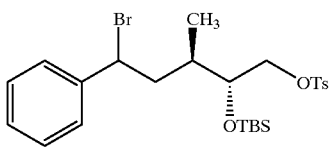

To a 5 L 3 neck round bottom flask equipped with a mechanical stirrer, reflux condenser and nitrogen inlet was added $CCl_4$ (1680 mL), TBS Ts (140 g, 0.30 mol), NBS (65 g, 0.365 mol) and AIBN (16.5 g, 0.10 mol). The mixture was degassed by evacuation under full vacuum with stirring, and backfilling with nitrogen (3×). The reaction mixture was then heated to reflux, whereupon the color became dark brown. After 15 min at vigorous reflux, the reaction mixture became light yellow, and chromatographic analysis indicated the reaction was complete. After cooling to room temperature, the reaction was filtered and the filtrate concentrated to dryness. The residue was redissolved in hexanes and filtered again, and concentrated to dryness to afford 170.3 gram as an amber oil.

Step 8. (2R, 3R)-2-[(tert-Butyldimethylsilyl)oxy]-3-methyl-5-phenylpent-4(E)-en-1-yl Tosylate

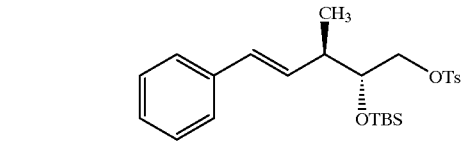

To a 2 L 3 neck round bottom flask equipped with a mechanical stirrer, reflux condenser and nitrogen inlet was added a solution of the bromide (100 g, 0.186 mol) in acetonitrile (700 mL). DBU (83.6 mL, 0.557 mol) was added and the resulting dark brown solution was stirred at reflux for 15 min. After cooling to room temperature, the solvent was removed in vacuo, and the residue digested in $CH_2Cl_2$ (200 mL) and filtered through a silica pad. The volatiles were again evaporated, and the residue dissolved in EtOAc and washed with water, brine and dried over $MgSO_4$ and concentrated to dryness. Preparative mplc (Prep 500) chromatography afforded the desired unsaturated compound (50.3 g, 60% yield over 4 steps).

Step 9. (3S, 4R)-3-[(tert-Butyldimethylsilyl)oxy]-4-methyl-6-phenylhex-5(E)-en-1-nitrile

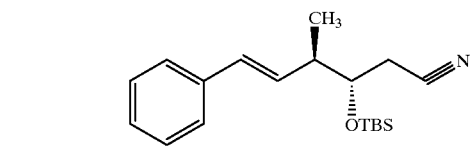

The tosylate (50 g, 0.11 mol) was dissolved in DMSO (1 L) and treated with KCN (14.2 g, 0.22 mol) and water (25 mL), and the resulting mixture was stirred at 60° C. under nitrogen for 18 h. After cooling to room temperature, the reaction mixture was partitioned between EtOAc (1 L) and water (1 L). The aqueous phase was extracted with EtOAc (500 mL), and the combined organic phase was washed with brine and dried over $Na_2SO_4$. Flash chromatography over silica with $CH_2Cl_2$ afforded the desired nitrile in 92% yield.

Step 10. Methyl (5S, 6R)-5-[(tert-Butyldimethylsilyl)oxy]-6-methyl-8-phenylocta-2(E),7(E)-dienoate

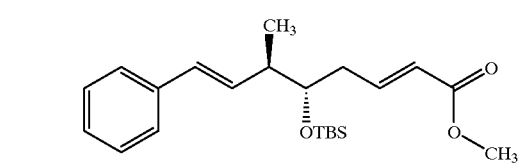

The nitrile (14.67 g, 46.5 mmol) was dissolved in toluene (200 mL) and cooled to −78° C. under nitrogen. A 1.5M solution of DIBAL in toluene (37.2 mL, 55.8 mmol) was added dropwise with vigorous stirring. Upon complete addition, the cooling bath was removed and the reaction was stirred at room temperature for 1 h. The reaction mixture was carefully poured into 1N HCl and the mixture stirred at room temperature for 30 min. The layers were separated, and the organic phase was washed with a saturated aqueous solution of sodium potassium tartrate (2×), brine and dried over $Na_2SO_4$. The volatiles were removed in vacuo, and the crude pale yellow oil was used directly in the subsequent condensation.

The crude aldehyde from above was dissolved in THF (90 mL) and treated with trimethyl phosphonoacetate (9.03 mL, 55.8 mmol) and tetramethylguanidine (7.0 mL, 55.8 mmol) at room temperature under nitrogen. The reaction mixture was stirred for 16 h, then partitioned between EtOAc (200 mL) and water (100 mL). The aqueous phase was back extracted with EtOAc (100 mL), and the combined organic phase was washed with water, brine and dried over $Na_2SO_4$. The volatiles were removed in vacuo, and the crude yellow oil (17.0 g) was chromatographed over silica gel with $CH_2Cl_2$:cyclohexane (1:1 to 2:1) to afford 13.67 grams of the desired ester, 78.5%.

Preparation 2
(5S,6R)-5-[(tert-Butyldimethylsilyl)oxy]-6-methyl-8-phenylocta-2(E),7(E)-dienoic acid

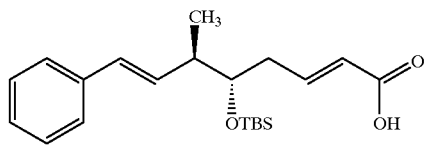

Methyl (5S, 6R)-5-[(tert-Butyldimethylsilyl)oxy]-6-methyl-8-phenylocta-2(E),7(E)-dienoate from Preparation 1, step 10 (1.00 g, 2.673 mmol) was dissolved in acetone (44 mL) and then 1N aqueous LiOH (26 mL) added at room temperature. The cloudy mixture was further diluted with acetone (20 mL) and the resulting yellow mixture stirred at room temperature for 23.5 h. The reaction was diluted with diethylether (400 mL) and the organics washed with 1N Hcl (120 mL), brine (200 mL) and $H_2O$ (160 mL). The organics were dried ($MgSO_4$) and concentrated in vacuo to leave a yellow oil which was purified by column chromatography (gradient elution: 5% AcOH+20%–40% EtOAc/Hexanes) to give carboxylic acid as a yellow oil (960 mg, 100%).

$[a]_D^{589}$ +87.6° (c 10.5, $CHCl_3$); $^1H$ NMR ($CDCl_3$) d 7.38–7.19 (m, $PhH_5$), 7.09 (ddd, J=15.2, 7.6 and 7.9 Hz, 3-H), 6.38 (d, J=16 Hz, 8-H), 6.16 (dd, J=16 and 8 Hz, 7-H), 5.85 (d, J=15.8 Hz, 2-H), 3.81–3.75 (m, 5-H), 2.49–2.37 (m, 6-H, 4-HH'), 1.12 (d, J=6.7 Hz, 6-Me), 0.91 (s, 9H, $SiCMe_3$), 0.065 (s, SiMe), 0.068 (s, SiMe) ppm; IR ($CHCl_3$) $l_{max}$ 2957, 2930, 2858, 1697, 1258, 1098, 838 $cm^{-1}$; MS (FD) 360.2 (M+,100); Anal. calcd. for $C_{21}H_{32}O_3$ requires: C,69.95; H,8.95%. Found: C,69.19; H,8.39%.

Preparation 3

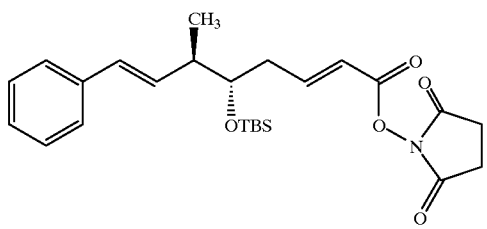

To a stirred solution of the carboxylic acid of Preparation 2 (720 mg, 2 mmol) in dry dimethylformamide (5.50 mL) was added 1-Ethyl-3-(3-dimethyaminopropyl)carbodiimide (459 mg, 2.4 mmol) and N-hydroxy-succinimide (299 mg, 2.6 mmol) at room temperature. The mixture was stirred for 28 h and then diluted with EtOAc (100 mL) and washed with 1N aqueous HCl (2×50 mL), $H_2O$ (75 mL), dried (MgSO4) and concentrated in vacuo to leave an oil. Crude product was purified by column chromatography (gradient elution: 5–30% EtOAc/Hexanes) to give active ester as a pale yellow oil (724 mg,80%).

$[a]_D^{589}$ +71.3° (c 10.1, $CHCl_3$); $^1H$ NMR ($CDCl_3$) d 7.36–7.20 (m, $PhH_5$, 3-H), 6.38 (d,J=16 Hz, 8-H), 6.14 (dd, J=16.1 and 8.0 Hz, 7-H), 6.03 (d, J=16 Hz, 2-H), 3.79 (q, J=4.3 Hz, 5-H), 2.94 (brs, $CH_2CH_2$), 2.58–2.42 (m, 6-H, 4-HH'), 1.10 (d,J=6.8 Hz, 6-Me), 0.90 (s, 9H, $SiCMe_3$), 0.05 (s, 6H, $SiMe_2$) ppm; IR ($CHCl_3$) $l_{max}$ 2957, 2931, 2858, 1772, 1741, 1648, 1364, 1254, 1092, 1069, 838 $cm^{-1}$; MS (FD) 457 (M+,100); Anal. calcd. for $C_{25}H_{35}NO_5$ requires: C,65.61;H,7.71;N,3.06%. Found: C,65.51;H,7.56; N, 3.02%.

Preparation 4

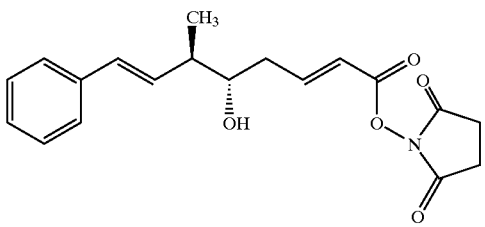

To a stirred solution of active ester of Preparation 3 (2.50 g,5.47 mmol) in $CH_3CN$ (130 mL) was added 48% aqueous HF (15 mL) at 0 C. The solution was stirred at 0 C. for 0.75 h and then at room temperature for 4 h. The reaction was diluted with diethylether (300 mL) and washed with $H_2O$ until the wash was ~pH7. Organics were dried ($MgSO_4$) and concentrated in vacuo to give a yellow residue which was recrystallized from Et2O to give alcohol as white crystals (1.46 g,78%). $^1H$ NMR ($CDCl_3$) d 7.41–7.20 (m,$PhH_5$,3-H), 6.48 (d,J=16 Hz,8-H), 6.15–6.07 (m,7-H,2-H), 3.71–3.65 (m,5-H), 2.83 (brs,$CH_2CH_2$), 2.60–2.33 (m,6-H,4-$CH_2$), 1.95 (brs, 5-OH), 1.14 (d,J=6.8 Hz,6-Me) ppm; IR u (KBr) 3457,1804,1773,1735,1724,1209,1099,1067,1049,975, 744, 694 $cm^{-1}$; UV (EtOH) $l_{max}$ 250 (e=20535) nm; MS (FD) 343.2 (M+,100); $[a]_D$ −57.8° (c 10.56, $CHCl_3$); Anal. calcd. for $C_{19}H_{21}NO_5S$ requires: C,66.46;H,6.16;N,4.08%. Found: C,66.49; H,6.16; N, 4.07%.

Preparation 5

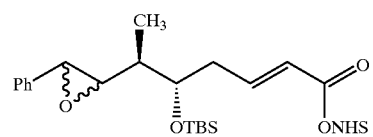

Acetone (10 mL) was added to a solution of the active ester of Procedure 3 (2.90 g, 6.35 mmol) in dichloromethane (20 mL) and the solution cooled to 0° C. An aqueous solution of oxone (11.7 g, 19 mmol) in $H_2O$ (30 mL) was slowly added to stirred solution of aqueous $NaHCO_3$ (5.3 g, 63.5 mmol) in $H_2O$ (30 mL) (gas evolution observed!). The resulting solution was added to the reaction mixture and stirred at 0° C. for 7 h (tlc- 50% conversion). Further oxone (6 g) and acetone (15 mL) were added and the mixture stirred for 1.5 h (tlc- all SM consumed). The reaction mixture was diluted with $H_2O$ (5 volumes) and product extracted with $CH_2Cl_2$ (5×100 mL). Combined, dried ($MgSO_4$) organics were concentrated in vacuo to give product as a yellow gummy solid (2.88 g). Tlc and $^1H$ NMR indicated 90% desired epoxide product (a:b=1:1.62): 10% SM. Crude product was purified by column chromatography ($SiO_2$:gradient elution:15%–25% EtOAc:Hexanes) to give recovered styrene (389 mg, 13%) and epoxide as a yellow oil (2.38 g, 80%). Epoxides (2 g, a:b=1:1.50) were separated by HPLC to give b-epoxide as a white crystalline solid (1.17 g, 59%. 99.8% ee) and a-epoxide as white crystalline solid (0.864 g, 43.2%, 99% ee).

Preparation 6

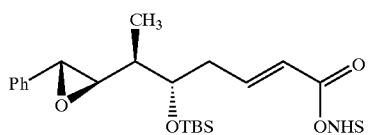

HPLC: C18 reverse phase, flow rate 1 mL/min, 60:40-CH$_3$CN:H$_2$O, l=254 nm, b-epoxide Rt=17.2 mins (AUC 1.5); [a]$_D^{589}$ +77.36 (c 1.06, CH$_2$Cl$_2$); $^1$H NMR (CDCl$_3$) d 7.35–7.24 (m, 6H, ArH$_5$, 3-H), 6.08 (d, J=15.8 Hz, 2-H), 3.91–3.88 (m, 5-H), 3.70 (s, 8-H), 2.97 (dd, J=6 and 0.9 Hz, 7-H), 2.85 (s, 4H, CH$_2$CH$_2$), 2.56–2.51 (m, 4-HH'), 1.78–1.76 (m, 6-H), 1.06 (d, J=6.9 Hz, 6-Me), 0.86 (s, 6H, SiCMe$_3$), 0.05 (s, SiMe), 0.01 (s, SiMe) ppm; IR (CHCl$_3$) u 2957, 2931, 1742, 1773, 1200, 1069, 839 cm$^{-1}$; UV (EtOH) l$_{max}$ 217 (e=21180) nm; MS (FD) m/z 474 (M$^+$, 10), 416 ([M-CMe$_3$]$^+$, 100); Anal. calcd. for C$_{25}$H$_{35}$NO$_6$ requires: C, 63.40; H, 7.45; N, 2.96%. Found: C, 63.45; H, 7.31; N, 3.21%.

Preparation 7

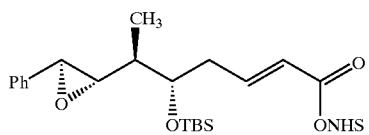

HPLC: C18 reverse phase, flow rate 1 mL/min, 60:40-CH$_3$CN:H$_2$O, l=254 nm, a-epoxide Rt=21.0 mins (AUC 1.0); [a]$_D^{589}$ +10.68° (c 1.03, CH$_2$Cl$_2$); $^1$H NMR (CDCl$_3$) d 7.38–7.26 (m, 6H, ArH$_5$, 3-H), 6.13 (d, J=15.7 Hz, 2-H), 3.94–3.89 (m, 5-H), 3.60 (s, 8-H), 2.99 (dd, J=7.3 and 1.3 Hz, 7-H), 2.85 (s, 4H, CH$_2$CH$_2$), 2.76–2.71 (m, 4-H), 2.61–2.54 (m, 4-H'), 1.64 (dt, J=7.2 and 2.8 Hz, 6-H), 1.03 (d, J=7 Hz, 6-Me), 0.90 (s, 9H, SiMe$_3$), 0.08 (s, SiMe), 0.05 (s, SiMe) ppm; IR (CHCl$_3$) u 2957, 2931, 1741, 1773, 1649, 1254, 1200, 1125, 1095, 1069, 891, 839 cm$^{-1}$; UV (EtOH) l$_{max}$ 218 (e=21727) nm; MS (FD) m/z 474 (M$^+$, 10), 416 ([M-CMe$_3$]$^+$, 100); Anal. calcd. for C$_{25}$H$_{35}$NO$_6$ requires: C, 63.40; H, 7.45; N, 2.96%. Found: C, 63.20; H, 7.63; N, 3.07%.

Preparation 8

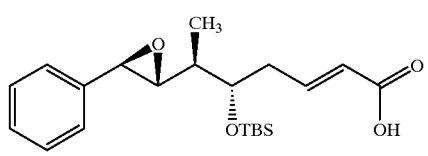

Preparation of β-Epoxy Fragment A Acid

A solution of 2a' (1.91 g, 5.30 mmol) of the formula

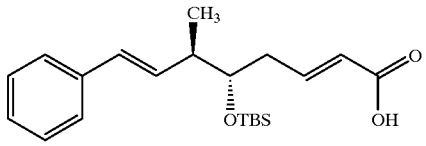

in CH$_2$Cl$_2$ (18 mL) was treated with m-chloroperbenzoic acid (0.96 g, 5.6 mmol) and the mixture stirred for 4 h before the volatiles were evaporated to give a colorless oil (2.88 g). Preparative HPLC was used to separate the epoxides (1.2:1 β:α) to give the desired β-epoxide as a colorless solid (42%). $^1$H NMR (500 MHz, CDCl$_3$) δ 7.37–7.27 (m, 5H), 7.11 (ddd, 1H, J=15.5, 7.6, 7.6 Hz), 5.92 (d, 1H, J=15.5 Hz), 3.90 (ddd, 1H, J=5.6, 5.6, 5.4 Hz), 3.70 (d, 1H, J=2.0 Hz), 3.00 (dd, 1H, J=6.6, 2.1 Hz), 2.51 (dd, 2H, J=6.5, 6.5 Hz), 1.77–1.73 (m, 1H), 1.10 (d, 3H, J=6.8 Hz), 0.89 (s, 9H), 0.07 (s, 3H), 0.03 (s, 3H). MS (FD) m/z 377 (M+1, 43), 319 (M-57, 100).

Preparation 9

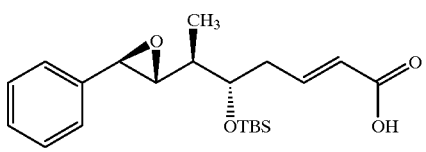

Alternate Preparation of β-Epoxy Fragment A Acid

To a stirred solution of acid 2a' (100 mg, 0.277 mmol) in CH$_3$CN (3.7 mL) at 0° C. was added a solution of Na$_2$EDTA (1×10$^{-4}$ M in H$_2$O, 2.8 mL, 0.28 μmol) and tetrabutylammonium hydroxide (1 M in MeOH, 28 μL, 28 μmol). After NaHCO$_3$ (23.3 mg, 0.277 mmol) was added, the pH was adjusted to 8.0 with 2 M NaOH and a mixture of Oxone (1.70 g, 2.77 mmol) and NaHCO$_3$ (722 mg, 8.59 mmol) prepared. A 100 mg portion of the Oxone/NaHCO$_3$ was added followed by ketone (7) (143 mg, 0.554 mmol). The pH was immediately adjusted to 7.8–8.0 with 2 M NaOH. The rest of the Oxone/NaHCO$_3$ mixture was added in 95 mg portions in 10 min intervals and a solution of (7) (143 mg, 0.554 mmol) in CH$_3$CN (500 μL) was added to the mixture during this period via a syringe pump. Throughout the experiment the pH was maintained at 7.8–8.0 with 2 M NaOH and 1 N H$_2$SO$_4$. HPLC analysis (C18 reverse phase, detection at 220 nm, flow rate at 1 mL/min, CH$_3$CN (0.05% TFA)/H$_2$O (0.05% TFA)-% CH$_3$CN: 80% to 90% over 10 min) 3 h after the Oxone addition revealed that the conversion was greater than 95% with a β/α epoxide ratio of 5.0:1. The mixture was filtered and the wetcake washed with CH$_2$Cl$_2$ (15 mL). The filtrate was washed with H$_2$O (15 mL) and the aqueous phase back extracted with CH$_2$Cl$_2$ (15 mL). The combined organic phases were washed with 0.1 M HCl (10 mL) and H$_2$O (10 mL), dried (MgSO$_4$), and concentrated to give the crude product as a yellow oil (104 mg, 100%).

37

Preparation 10

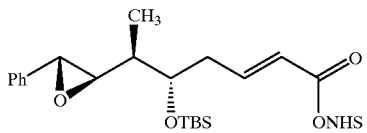

Alternate Preparation of β-Epoxy Fragment A N-Hydroxysuccinimide Ester

The epoxidation of N-hydroxysuccinimide ester of Preparation 3 (127 mg, 0.277 mmol) was performed in the same manner as described in Preparation 9 except that the pH was lowered to 5.6 with 1 N $H_2SO_4$ after the tetrabutylammonium hydroxide was added, prior to addition of sodium bicarbonate. HPLC analysis (same method as used for the analysis used in Preparation 9) 3.5 h after the Oxone addition revealed that the conversion was greater than 95% with a β/α epoxide ratio of 6.3:1. After $CH_2Cl_2$ (6 mL) was added, the mixture was filtered and the wetcake washed with $CH_2Cl_2$ (14 mL). The filtrate was washed with $H_2O$ (10 mL) and the aqueous phase back extracted with $CH_2Cl_2$ (2×20 mL). The combined organic phases were dried ($MgSO_4$) and concentrated to a colorless oil. Chromatography on silica gel with EtOAc/hexane (1:3) gave the title compound as colorless solid (8:1 β/α epoxide mixture, 82 mg, 63%).

Preparation 11

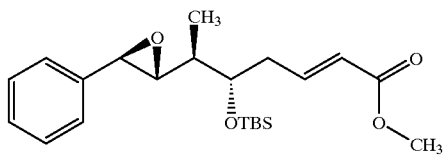

Preparation of β-Epoxy Fragment A Methyl Ester

The epoxidation of the methyl ester of Preparation 1, step 10 (104 mg, 0.278 mmol) was performed in the same manner as described in Preparation 9 except that the pH was lowered to 3.3 with 1 N $H_2SO_4$ after the tetrabutylammonium hydroxide was added, prior to the addition of sodium bicarbonate. HPLC analysis (same method as used for the analysis of the product of Preparation 9 except % $CH_3CN$: 95%, isocratic) 2 h after the Oxone addition revealed that conversion was greater than 95% with a β/α epoxide ratio of 4.9:1. After $CH_2Cl_2$ (6 mL) was added, the mixture was filtered and the wetcake washed with $CH_2Cl_2$ (14 mL). The filtrate was washed with $H_2O$ (10 mL) and the aqueous phase back extracted with $CH_2Cl_2$ (2×20 mL). The combined organic phases were dried ($MgSO_4$) and concentrated to give the crude product as a yellow oil (123 mg, 113%). $^1H$ NMR (500 MHz, $CDCl_3$) δ 7.38–7.26 (m, 5H), 6.99 (ddd, 1H, J=15.8, 7.6, 7.6 Hz), 5.91 (d, 1H, J=15.8 Hz), 3.87 (ddd, 1H, J=5.6, 5.6, 5.4 Hz), 3.75 (s, 3H), 3.70 (d, 1H, J=2.1 Hz), 3.00 (dd, 1H, J=6.8, 2.1 Hz), 2.49–2.45 (m, 2H), 1.75–1.69 (m, 1H), 1.10 (d, 3H, J=6.8 Hz), 0.88 (s, 9H), 0.06 (s, 3H), 0.02 (s, 3H). MS (FD) m/z 391 (M+1, 8), 333 (M-57, 100).

38

Preparation 12

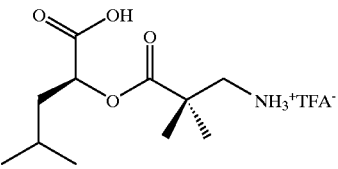

Boc amine (1.69 g,5.09 mmols) of the formula

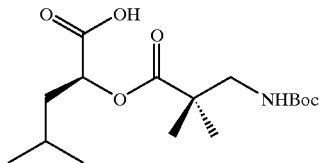

PCT Intnl. Publ. No. WO 97/07798, published Mar. 6, 1997; was dissolved in trifluoroacetic acid (17 ml) and the solution stirred at room temperature under a dry nitrogen atmosphere for 4.75 h and then concentrated in vacuo and dried under high vacuum for 24 h to give the amine salt as a yellow viscous oil (1.76 g, 100%).
$[\alpha]_D^{589}$ -11.54° (c 1.04, MeOH); $^1H$ NMR ($CDCl_3$) δ Unit C': 7.43 (br s, 3H, $NH_3^+$),3.34–3.28 (m, 3-H), 3.18–3.12 (m, 3-H'), 1.42 (s, 2-Me), 1.36 (s, 2-Me); Unit D: 10.94 (br s, $CO_2H$), 5.23–5.20 (m, 2-H),1.92–1.77 (m, 3H, 3-HH', 4-H), 1.10 (d, J=5.8 Hz, 5-$H_3$), 0.98 (d, J=5.8 Hz, 4-Me) ppm; IR ($CHCl_3$) ν 2963, 1746, 1710, 1678, 1192, 1172 $cm^{-1}$; MS (FAB) 232.2 ([M+1]$^+$, 100).

Preparation 13

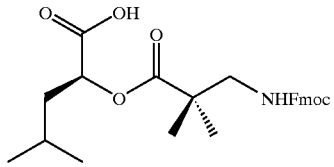

To a stirred solution of amine salt of Preparation 12 (5.09 mmols) in dioxane (20 mL) was added sodium bicarbonate (2.14 g,25.5 mmols) followed by FmocCl (1.58 g,6.11 mmols) at room temperature. The mixture was diluted with $H_2O$ (4 mL) and stirred for 19 h. The reaction mixture was quenched in 1N aqueous HCl (150 mL) and extracted with EtOAc (2×100 mL). Combined organics were washed with $H_2O$ (100 mL), dried ($MgSO_4$) and concentrated in vacuo to give a yellow gummy solid. The crude product was purified by column chromatography (Biotage-$SiO_2$: gradient elution; 10%–75% EtOAC: Hexanes) to provide Fmoc amine as a pale yellow solid (850 mg, 37%). Product was contaminated with amino acid, which was removed by dissolving the product in EtOAc and stirring with 1N HCl aq for several hours. Organics were dried and concentrated to give product (85:15 product: amino acid).
$[\alpha]_D^{589}$ -15.95° (c 0.50, $CH_2Cl_2$); $^1H$ NMR ($CDCl_3$) δ Unit C': 7.59 (d, J=7.4 Hz,$ArH_2$), 7.67–7.61 (m, $ArH_2$), 7.43 (t, J=7.3 Hz, $ArH_2$), 7.36–7.30 (m, $ArH_2$), 5.88 (t, J=5.8 Hz, NH), 4.41–4.38 (m, 3'-HH'), 4.35–4.28 (m,4'-H), 3.42 (d, J=6.5 Hz, 3-HH'), 1.27 (s, 2Me), 1.26 (s, 2-Me); Unit D: 8.40 (br s, CO2H), 5.18–5.13 (m, 2-H), 1.87–1.69 (m, 3H, 3-HH', 4-H), 0.97 (d, J=5,8 Hz, 5-H3), 0.93 (d, J=6.1 Hz, 4-Me)

ppm; IR (KBr) v 2959, 2937, 1730, 1540, 1471, 1451, 1307, 1268, 1145, 1128, 759, 741 cm$^{-1}$; UV (EtOH) $\lambda_{max}$ 299 (e=5851), 288 (e=4773), 265 (e=18369), 227 (e=4813) nm; MS (FAB) 454 ([M+1]$^+$, 26); Anal. calcd. for $C_{26}H_{31}NO_6$ requires: C, 68.86; H, 6.89; N, 3.09%. Found: C, 68.92; H, 7.01; N, 3.34%.

Preparation 14

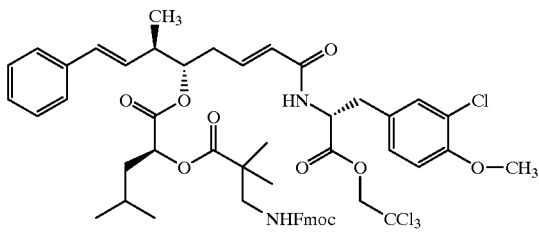

Preparation of Fmoc Seco

To a mixture of a fragment A-B compound (4')

(4')

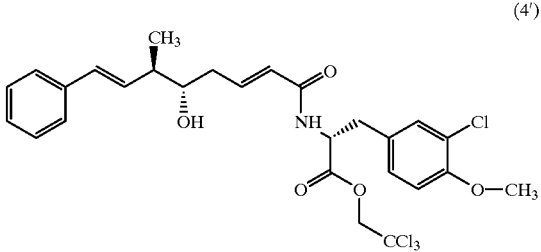

(600 mg, 1.01 mmol, Barrow, R. A. et al., *J. Am. Chem. Soc.* 117, 2479–2490 (1995)), a compound of Preparation 13 (618 mg, 1.36 mmol), and DMAP (24.7 mg, 0.202 mmol) in $CH_2Cl_2$ (3.6 mL) at 0° C. was added a solution of DCC (281 mg, 1.36 mmol) in $CH_2Cl_2$ (1.2 mL) and the reaction was allowed to stir 5 min at 0° C. and 30 min at rt. After the mixture was diluted with EtOAc/hexane (1:1, 15 mL), it was filtered through Celite and the cake washed with EtOAc/hexane (1:1, 15 mL). The filtrate was washed with 1 M HCl (10 mL), saturated $NaHCO_3$ solution (10 mL), brine (10 mL), dried ($MgSO_4$), and concentrated to a yellow foam. Chromatography on silica gel with EtOAc/hexane (1:2.5 to 1:1) gave the title compound as a colorless foam (864 mg, 83.5%). $^1$H NMR (500 MHz, CDCl$_3$) δ 7.78 (d, 2H, J=7.5 Hz), 7.69–7.66 (m, 2H), 7.40 (dd, 2H, J=7.5, 7.4 Hz), 7.34–7.22 (m, 7H), 7.19 (d, 1H, J=1.8 Hz), 7.05 (dd, 1H, J=8.5, 1.8 Hz), 6.86–6.80 (m, 1H), 6.82 (d, 1H, J=8.4 Hz), 6.45 (d, 1H, J=8.4 Hz), 6.44 (d, 1H, J=15.5 Hz), 6.11–6.03 (m, 2H), 5.91 (d, 1H, J=15.7 Hz), 5.18 (m, 1H), 5.08–5.01 (m, 2H), 4.77 and 4.67 (AB quartet, 2H, J=11.9 Hz), 4.43–4.33 (m, 2H), 4.27 (dd, 1H, J=7.4, 7.2 Hz), 3.86 (s, 3 H), 3.43 (d, 2H, J=6.6 Hz), 3.21 (dd, 1H, J=14.1, 5.7 Hz), 3.07 (dd, 1H, J=14.2, 6.7 Hz), 2.69–2.58 (m, 3H), 1.79–1.72 (m, 2H), 1.67–1.61 (m, 1H), 1.29 (s, 3H), 1.20 (s, 3H), 1.17 (d, 3H, J=6.8 Hz), 0.91 (d, 3H, J=6.4 Hz), 0.87 (d, 3H, J=6.4 Hz). Anal. Calcd for $C_{53}H_{58}Cl_4N_2O_{10}$: C, 62.11; H, 5.70; N, 2.73. Found: C, 62.21; H, 5.68; N, 2.50.

Example 1

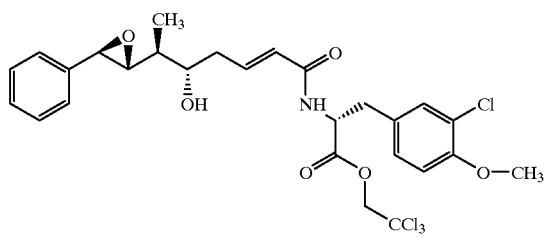

Preparation of β-Epoxy Fragment A-B

The epoxidation of fragment A-B of formula (4') (653 mg, 1.11 mmol, Barrow, R. A. et al., *J. Am. Chem. Soc.* 117, 2479–2490 (1995)) was performed in the same manner as described in Procedure 9 except that the pH was lowered to 4.4 with 1 N $H_2SO_4$ after the tetrabutylammonium hydroxide was added, prior to addition of sodium bicarbonate. The reaction was complete before all of the Oxone/NaHCO$_3$ mixture and ketone were added. HPLC analysis (same method as used for the analysis of the product of Procedure 9 except % $CH_3CN$: 70% to 85% over 15 min) revealed that the Fragment A-B starting material was consumed to give a 5:1 β/α epoxide mixture after 80% of the Oxone/NaHCO$_3$ mixture had been added (1.6 equivalents of the 2 equivalents of (7) which were added slowly had been added). After $CH_2Cl_2$ (24 mL) was added, the mixture was filtered and the wetcake washed with $CH_2Cl_2$ (56 mL). The filtrate was washed with $H_2O$ (40 mL) and the aqueous phase back extracted with $CH_2Cl_2$ (2×40 mL). The combined organic phases were dried ($MgSO_4$) and concentrated to give the crude product as a light yellow foam (798 mg, 119%), which was used directly in the next reaction without purification. $^1$H NMR (500 MHz, CDCl$_3$) δ 7.39–7.29 (m, 5H), 7.21 (d, 1H, J=2.2 Hz), 7.06 (dd, 1H, J=8.4, 2.1 Hz), 6.93 (ddd, 1H, J=15.4, 7.4, 7.4 Hz), 6.88 (d, 1H, J=8.4 Hz), 5.94 (d, 1H, J=15.4 Hz), 5.90 (d, 1H, J=7.8 Hz), 5.09 (ddd, 1H, J=7.7, 6.0, 5.9 Hz), 4.82 and 4.76 (AB quartet, 2H, J=11.8 Hz), 3.90 (s, 3H), 3.83 (d, 1H, J=2.1 Hz), 3.78–3.74 (m, 1H), 3.25 (dd, 1H, J=14.2, 5.9 Hz), 3.15 (dd, 1H, J=14.2, 6.0 Hz), 3.02 (dd, 1H, J=6.7, 2.1 Hz), 2.58–2.52 (br m, 1H), 2.39 (ddd, 1H, J=14.8, 7.6, 7.6 Hz), 1.79 (m, 1H), 1.14 (d, 3H, J=6.9 Hz). MS (FD) m/z 603 (M$^+$).

Example 2

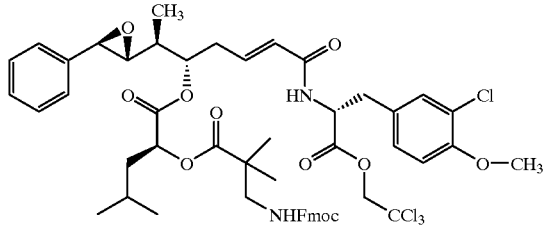

Preparation of β-Epoxy Fmoc Seco from Fmoc Seco

To a stirred solution of a compound of Preparation 14 (382 mg, 0.373 mmol) in $CH_3CN$ (4.7 mL) at 0° C. was added a solution of Na$_2$EDTA (1×10$^{-4}$ M in $H_2O$, 3.7 mL, 0.37 μmol) and tetrabutylammonium hydroxide (1 M in MeOH, 37 μL, 37 μmol). The pH was lowered to 3–6 with 1 N $H_2SO_4$ before $NaHCO_3$ (31.3 mg, 0.373 mmol) was added. After a mixture of Oxone (2.29 g, 3.72 mmol) and $NaHCO_3$ (975 mg, 11.6 mmol) was prepared, the pH was adjusted to 8.2 with 1 N $H_2SO_4$ and the ketone (7) (385 mg, 1.49 mmol) added. The Oxone/NaHCO$_3$ mixture was then added in 128 mg portions in 10 min intervals and the pH maintained at 7.8–8.2 with 2 M NaOH and 1 N H$_2$SO$_4$. HPLC analysis (same method as used for the analysis of the product of Procedure 9 except % CH$_3$CN: 95%, isocratic) 1 h after the Oxone addition revealed that the conversion was 85% with a β/α epoxide ratio of 9.5:1. After CH$_2$Cl$_2$ (8 mL) was added, the mixture was filtered and the wetcake washed with CH$_2$Cl$_2$ (19 mL). The filtrate was washed with H$_2$O (13 mL) and the aqueous phase back extracted with CH$_2$Cl$_2$ (2×27 mL). The combined organic phases were dried (MgSO$_4$) and concentrated to give the crude product as a beige foam (375 mg, 97%).

Example 3

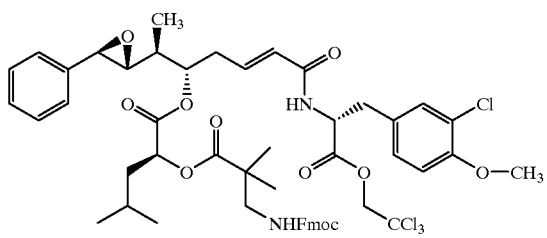

Preparation of β-Epoxy Fmoc Seco from β-Epoxy Fragment A-B

A solution of the epoxide product of Example 1 (788 mg, 1.09 mmol theory) in CH$_2$Cl$_2$ (3.7 mL) was added to the acid of Preparation 13 (742 mg, 1.64 mmol) followed by DMAP (26.6 mg, 0.218 mmol), and the mixture was immediately cooled to 0° C. After a solution of DCC (338 mg, 1.64 mmol) in CH$_2$Cl$_2$ (1.2 mL) was added, the mixture was allowed to stir for 5 min at 0° C. and for 1 h at rt. The mixture was then diluted with EtOAc/hexane (1:1, 20 mL), filtered through Celite, and concentrated to a yellow foam. Chromatography on silica gel with EtOAc/hexane (1:3 to 1:2) gave the title compound as a light yellow foam (7.8:1 β/α epoxide mixture, 772 mg, 68% from Fragment A-B corrected to 55% due to contamination by byproduct). $^1$H NMR (500 MHz, CDCl$_3$) δ 7.77 (d, 2H, J=7.5 Hz), 7.66–7.60 (m, 2H), 7.40–7.24 (m, 9H), 7.19 (s, 1H), 7.05 (d, 1H, 8.4 Hz), 6.86–6.79 (m, 1H), 6.82 (d, 1H, J=8.4 Hz), 6.44 (d, 1H, J=8.0 Hz), 5.98–5.94 (br m, 1 H), 5.91 (d, 1H, J=15.6 Hz), 5.23–5.20 (m, 1H), 5.09–5.04 (m, 1H), 5.0 (dd, 1H, J=9.8, 3.2 Hz), 4.77 and 4.68 (AB quartet, 2H, J=11.8 Hz), 4.43–4.34 (m, 2H), 4.27–4.23 (m, 1H), 3.85 (s, 3H), 3.73 (d, 1H, J=1.7 Hz), 3.44–3.38 (m, 2H), 3.20 (dd, 1H, J=14.2, 5.7 Hz), 3.07 (dd, 1H, J=14.2, 6.7 Hz), 2.94 (dd, 1H, J=6.9, 1.7 Hz), 2.66–2.57 (m, 2H), 1.97–1.90 (m, 1H), 1.80–1.71 (m, 2H), 1.60–1.55 (m, 1H), 1.25 (s, 3H), 1.19 (s, 3H), 1.15 (d, 3H, J=6.9 Hz), 0.93 (d, 6H, J=6.4 Hz), MS (FD) m/z 1038 (M$^+$).

Example 4

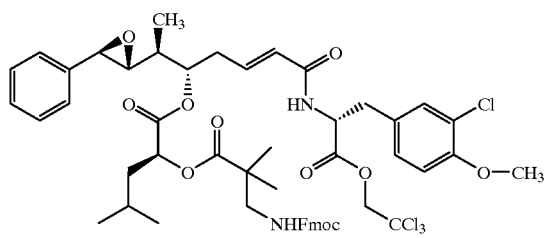

Preparation of β-Epoxy Fmoc Seco from Fragment A-B: Epoxidation at pH 10.5 followed by coupling with preactivation of Fmoc C'D Acid Epoxidation: To a stirred mixture of fragment A-B (4') (650 mg, 1.10 mmol), sodium tetraborate buffer (0.05 M in 4×10$^{-4}$ M aqueous Na$_2$EDTA, 11.2 mL), tetrabutylammonium hydrogen sulfate (14.9 mg, 43.9 μmol), and ketone (7) (568 mg, 2.20 mmol) in CH$_3$CN (16.8 mL) at 0° C. was added a solution of Oxone (2.61 g, 4.24 mol) in aqueous Na$_2$EDTA (4×10$^{-4}$ M, 20 mL) and a solution of K$_2$CO$_3$ (0.89 M, 20 mL) over 2 h. HPLC analysis (same method as used for the analysis of the product of Preparation 9 except % CH$_3$CN: 70% to 85% over 15 min) at the end of the addition revealed that the conversion was >95% with a β/α epoxide ratio of 6.5:1. The mixture was diluted with CH$_2$Cl$_2$ (30 mL) and washed with H$_2$O (20 mL). The aqueous layer was back extracted with CH$_2$Cl$_2$ (2×30 mL) and the combined organic layers were dried (MgSO$_4$) and concentrated to faint yellow foam (995 mg) which was taken into the next step without further purification. Coupling: To a solution of the acid (10a) (723 mg, 1.60 mmol) and DMAP (26.9 mg, 0.220 mmol) in CH$_2$Cl$_2$ (1.7 mL) at 0° C. was add a solution of the DCC in CH$_2$Cl$_2$ (1.3 mL). After the mixture was stirred for 5 min, a solution of the crude alcohol in CH$_2$Cl$_2$ (1.5 mL) was added and the reaction was stirred for 5 min at 0° C. and 1 h at rt. The mixture was then diluted with EtOAc/hexane (1:1, 20 mL), filtered through Celite, and concentrated to a yellow foam. Chromatography on silica gel with EtOAc/hexane (1:3 to 1:2) gave the title compound as a light yellow foam (10.3:1 β/α epoxide mixture, 820 mg, 71% contaminated with only 4% of byproduct).

Example 5

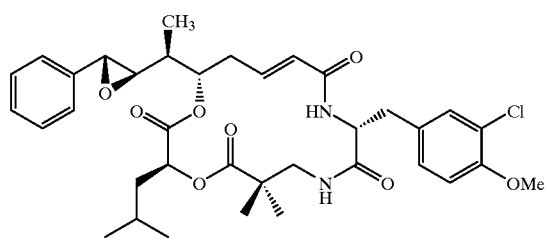

Preparation of Cryptophycin 52 from Cryptophycin 51

The epoxidation of Cryptophycin 51 (181 mg, 0.277 mmol) was performed in the same manner as described in Preparation 9 except that the pH was lowered to 7.8 with 1 N H$_2$SO$_4$ after the tetrabutylammonium hydroxide was added, prior to addition of sodium bicarbonate. HPLC analysis (same method as used for the analysis of the product of Preparation 9 except % CH$_3$CN: 60% to 90% over 20 min) near the end of the Oxone addition revealed that the conversion was less than 10% with a β/α epoxide ratio of 5–7:1.

Example 6

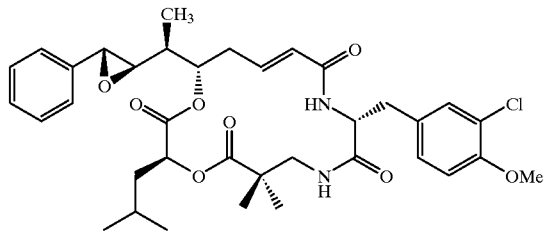

Preparation of Cryptophycin 52 from β-Epoxy Fmoc Seco

To a solution of β-Epoxy Fmoc Seco of Example 3 (767 mg, 0.737 mmol corrected to 0.54 mmol due to contamination by α-epoxide and byproduct) in DMF (74 mL) was added piperidine (364 μL, 3.69 mmol), and the reaction was allow to stir for 20 h before it was diluted with EtOAc (200 mL) and washed with H$_2$O (3×200 mL). The combined aqueous layers were back extracted with EtOAc (60 mL) and the combined organic layers dried (MgSO$_4$) and concentrated to an orange oil. Crystallization from toluene (2.5 mL, seeded with Cryptophycin 52) provided the title compound as a colorless solid (171 mg, 47%).

Example 7

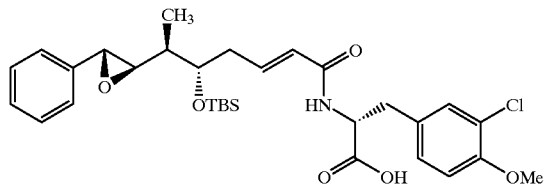

To a solution of β-epoxide of Preparation 6 (473 mg, 1.0 mmol) in dry DMF (6.7 mL) was added amino acid "B" (459 mg, 2.0 mmols), represented by the formula

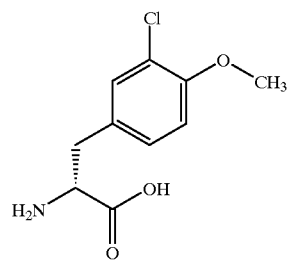

PCT Intnl. Publ. No. WO 97/07798, published Mar. 6, 1997; followed by N,O-bis-(trimethylsilyl)acetamide (618 uL, 2.5 mmols) at room temperature under a nitrogen atmosphere. The resulting mixture was heated at 55° C. (solution formed) for 8 h, diluted with EtOAc (250 mL) and washed with 1N aqueous HCl (3×80 mL), H$_2$O (100 mL). Combined, dried (MgSO$_4$) organics were concentrated in vacuo to give a yellow foam (590 mg), which further purified by column chromatography (SiO$_2$, gradient elution; CH$_2$Cl$_2$-5%–10% MeOH: CH$_2$Cl$_2$) to give silyl ether product as white foam (489 mg, 89%).

$[\alpha]_D^{589}$ +28.33° (c 1.06, MeOH); $^1$H NMR (DMSO-d6) δ Unit A: 7.33–7.17 (m, ArH$_5$), 6.55–6.40 (m, 3-H), 6.03 (d, J=15.3 Hz, 2-H), 3.83–3.76 (m, 5-H), 3.71 (s, 8-H), 2.90 (d, J=6.8 Hz, 7-H), 2.46–2.27 (m, 4-HH'), 1.50–1.44 (m, 6-H), 0.94 (d, J=6.7 Hz, 6-Me), 0.74 (s, 9H, SiMe$_3$), −0.54 (s, SiMe), −0.13 (s, SiMe); Unit B: 7.76 (d, J=7.3, NH), 7.33–7.17 m, ArH), 7.04 (d, J=8.5, ArH), 6.90 (d, J=8.5, ArH), 4.27–4.23 (m, 2-H), 3.72 (s, 3H, OMe), 3.02 (dd, J=13.3 and 4.3 Hz, 3-H), 2.78 (dd, J=13.5 and 7.8 Hz, 3-H') ppm; IR (KBr) u 2955, 2930, 2857, 1668, 1605, 1504, 1463, 1454, 1279, 1258, 1067, 1026, 837, 776 cm$^{-1}$; UV (EtOH) l$_{max}$ 278 (e=2219) nm.

Example 8

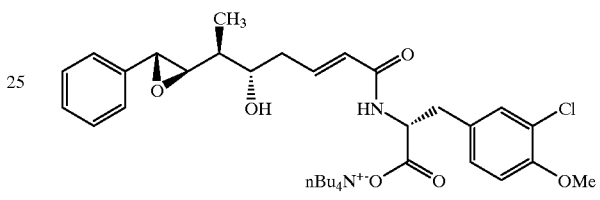

Method A

To a solution of silyl ether of Example 7 (160 mg, 0.272 mmols) in dry DMF (3.5mL) was added sodium bicarbonate (228 mg, 2.72 mmols) followed by solid tetrabutylammonium fluoride-hydrate (TBAF)(358 mg, 1.36 mmols). The mixture was heated at 60° C. for 17 h and then further TBAF (358 mg, 1.36 mmols) and heated for 9 h and finally a solution of 1M TBAF in THF (360 uL, 1.36 mmols) added turning the reaction a brown color. The mixture was heated for 20 mins and then the reaction quenched in water (100 mL) and extracted with EtOAc (3×50 mL). Combined, dried (Na$_2$SO$_4$) organics were concentrated in vacuo to give a brown oily gum (248 mg). Crude carboxylate salt was used in the next step without further purification.

Example 9

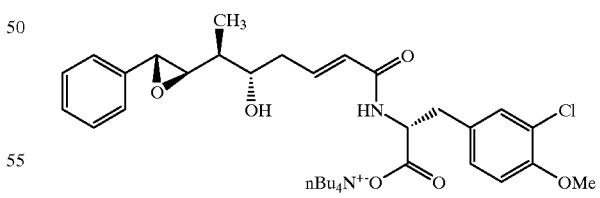

Method B

To a solution of silyl ether of Example 7 (145 mg, 0.247 mmols) in dry tetrahydrofuran (3.0 mL) was added a 1M solution of tetrabutylammonium fluoride (800 uL, 0.8 mmols) under a dry nitrogen atmosphere. The resulting solution was heated at 60° C. for 7 h and then worked-up as described above to give a brown residue (166 mg, 94%). Crude carboxylate salt was used in the next step without further purification.

Example 10

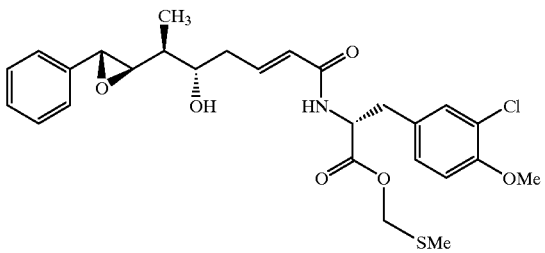

To a dry solution of crude carboxylate salt (0.272 mmols) in DMSO (3.5 mL) was sodium bicarbonate (274 mg, 3.26 mmols) followed by slow addition of a solution of t-butyl bromide (373 mg, 2.72 mmols) in DMSO (1.5 mL) over ~2 h at room temperature and under nitrogen. The mixture was stirred for a further 21 h and then quenched in brine (50 mL) and extracted with EtOAc (3×30 mL). Combined organics were washed with water (50 mL), dried ($Na_2SO_4$) and concentrated in vacuo to give crude ester as a gummy solid (117 mg, 81%). The crude alcohol A-B was used in the next step without further purification.

Example 11

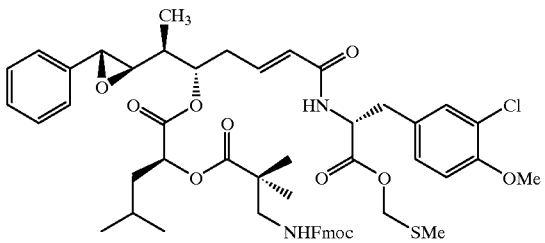

To a stirred solution of carboxylic acid D-C' of Preparation 13 (129 mg, 0.285 mmols) in dry dichloromethane (1.0 mL) was added DMAP (5.4 mg, 0.044 mmols) and DCC (59 mg, 0.285 mmols) at room temperature under a dry nitrogen atmosphere. The solution was stirred for 0.5 h and then solid sodium bicarbonate (37 mg, 0.44 mmols) added followed by a solution of crude alcohol A-B of Example 10 (117 mg, 0.22 mmols) in dry dichloromethane (1.2 mL). A precipitate formed within 10 mins and the mixture was stirred for a further 50 mins. The crude reaction mixture was directly applied onto a $SiO_2$ column and purified (gradient elution; 10%–40% EtOAc:Hexanes) to give methyl sulphide product as pale yellow solid (122 mg, 46% over 3 steps).

$^1$H NMR ($CDCl_3$) δ Unit A: 7.43–7.20 (m, $ArH_5$), 6.90–6.81 (m, 2H, 3-H, ArH), 5.93 (d, J=15.6 Hz, 2-H), 5.14–4.93 (m, 5-H), 3.05 (dd, J=14.5 and 8.3 Hz, 7-H), 2.65–2.63 (m, 4-HH'), 2.00–1.95 (m, 6-H), 1.17 (d, J=7.0, 6-Me); Unit B: 7.43–7.20 (m, ArH), 7.06 (d, J=8.1 Hz, ArH), 6.90–6.81 (m, ArH), 6.44 (d, J=7.7 Hz, NH), 5.19 (q, $J_{AB}$=11.8 Hz, 1'-HH), 5.14–4.93 (m, 2-H), 3.87 (s, OMe), 3.20–3.10 (m, 3-HH'), 2.21 (s, SMe); Unit C': 7.79 (d, J=7.4 Hz, $ArH_2$), 7.67 (d, J=6.9 Hz, $ArH_2$), 7.43–7.20 (m, $ArH_4$), 6.04 (d, J=7.7 Hz, NH), 4.42–4.34 (m, 3'-HH'), 4.30–4.25 (m, 4'-H, 3.42 (d, J=6.2 Hz, 3-HH'), 1.27 (s, 2-Me), 1.20 (s, 2-Me); Unit D: 5.22–5.18 (m, 2-H), 1.82–1.58 (m, 3H, 3-HH',4-H), 0.96 (s, 5-H3), 0.94 (s, 4-Me) ppm.

Example 12

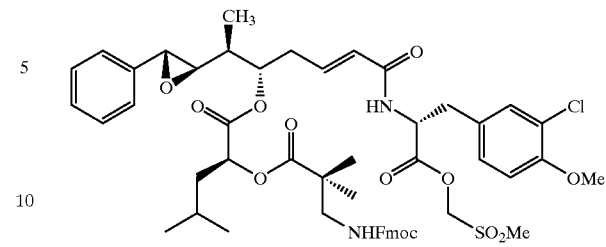

To a stirred solution of methyl sulphide of Example 11 (56 mg, 0.058 mmols) in acetone (10 mL) was added sodium bicarbonate (64 mg, 0.764 mmols) followed by an aqueous solution of oxone (234 mg, 0.382 mmols) in water (3.0 mL). The reaction mixture was stirred at room temperature for 20 mins (SM is rapidly converted to a very polar component sulphoxide and then with time to the less polar sulphone product). The reaction was quenched in water (40 mL) and extracted with EtOAc (3×20 mL). Organics were washed with brine (30 mL), dried ($MgSO_4$) and concentrated in vacuo to give a solid. Crude product was purified by column chromatography ($SiO_2$: gradient elution; 25%–60% EtOAc:Hexanes) to give sulphone as a white foamy solid (43 mg, 74%).

$^1$H NMR ($CDCl_3$) δ Unit A: 7.58–7.17 (m, $ArH_5$), 6.82–6.75 (m, 3-H), 5.87 (d, J=16 Hz, 2-H), 4.98–4.86 (m, 5-H), 3.70 (d, J=1.1 Hz, 7-H), 2.92–2.89 (m,7-H), 2.61–2.58 (m,4-HH'), 1.94–1.89 (m, 6-H), 1.13 (d, J=7.1 Hz, 6-Me); Unit B: 7.58–7.17 (m, ArH), 7.04 (d, J=7.7 Hz, ArH), 6.81 (d, J=8.1 Hz, ArH), 6.54 (d, J=7.5 Hz, NH), 4.98–4.86 (m, 2-H), 3.84 (s, 7-OMe), 3.17–2.98 (dq, $J_{AB}$=14 and 6.6 Hz, 2-HH'); Unit C': 7.75 (d, J=7.4 Hz, $ArH_2$), 7.62 (d, J=6.8 Hz, $ArH_2$), 7.58–7.17 (m, $ArH_4$), 5.97 (t, J=5.5 Hz, NH), 5.00 (s, $SO_2Me$), 4.98–4.86 (m, 2H, 1'-HH'), 4.38–4.33 (m, 3'-HH'), 4.25–4.20 (m, 4'-H), 3.40–3.36 (m, 3-HH'), 1.22 (s, 2-Me), 1.15 (s, 2-Me); Unit D: 5.19 (q, $J_{AB}$=5 Hz, 2-H), 1.80–1.61 (m, 2H, 3-H, 4-H), 1.57–1.49 (m, 3-H'), 0.91 (s, 5-$H_3$), 0.89 (s, 4-Me) ppm.

Example 13

Cryptophycin 52

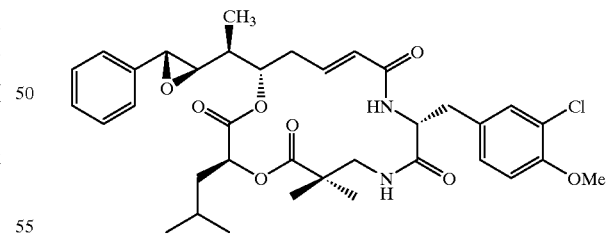

To a stirred solution of sulphone of Example 12 (18 mg, 17.98 umols) in dry DMF (2.0 mL) was added neat piperidine (8.9 uL, 90 umols) at room temperature and under nitrogen. The resulting solution was stirred for 5 h and then concentrated in vacuo to give crude amine as a foam. The amine was dissolved in toluene (3 mL) and heated at 60° C. under nitrogen for 40 mins. The reaction solution was directly purified by column chromatography ($SiO_2$; gradient elution; 20%–75% EtOAc:Hexanes) to give cryptophycin 52 as a white glass (6.1 mg, 51% over 2 steps).

¹H NMR (CDCl₃) δ Unit A: 7.45–7.38 (m, ArH₃), 7.31–7.23 (m, ArH₂), 6.85–6.76 (m, 3-H), 5.76 (d, J=15.6 Hz, 2-H), 5.27–5.23 (m, 5-H), 2.97 (dd, J=7.5 and 1.7 Hz, 7-H), 2.66–2.44 (m, 4-HH'), 1.86–1.67 (m, 6-H), 1.19 (d, J=6.9 Hz, 6-Me); Unit B: 7.31–7.23 (m, ArH), 7.09 (dd, J=8.3 and 2.0 Hz, ArH), 6.88 (d, J=8.4 Hz, ArH), 5.50 (d J=7.8 Hz, NH), 4.79 (q, J=6.4 Hz, 2-H), 3.92 (s, OMe), 3.73 (d, J=1.5 Hz, 8-H), 3.17–3.11 (m, 3-HH'); Unit C': 3.47 (dd, J=13.4 and 8.7 Hz, 3-H), 3.17–3.11 (m, 3'-H), 1.27 (s, 2-Me), 1.20 (s, 2-Me); Unit D: 4.87 (dd, J=10 and 3.3 Hz, 2-H), 1.86–1.67 (m, 2H, 3-H, 4-H), 1.40–1.30 (m, 3-H'), 0.88 (app t, J=6.3 Hz, 6H, 5-H₃, 4-Me) ppm.

Conversion rates and β/α ratios are presented in Table 1 below. Epoxidations were completed in CH₃CN/aq. H₂O at 0° C. and pH 7.8–8.2 using 4 equivalents of (7) (2 of the 4 equivalents added over 4 hours) and a mixture of Oxone (10 equivalents) and NaHCO₃ (31 equivalents) which was added over 4 hours. For entry 2, all of the ketone (7) was added at the beginning.

We claim:
1. A process for preparing a compound of the formula

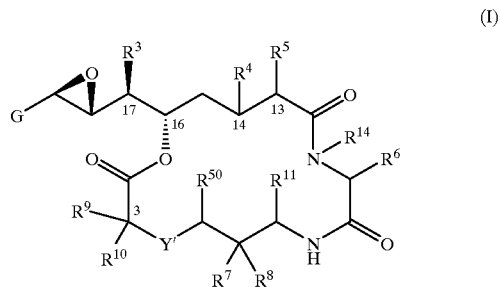

(I)

wherein
G is $C_1$–$C_{12}$ alkyl, $C_2$–$C_{12}$ alkenyl, $C_2$–$C_{12}$ alkynyl, or Ar;
Ar is an aromatic or heteroaromatic group or a substituted aromatic or heteroaromatic group;

TABLE 1

Asymmetric Epoxidation of Cryptophycin Intermediates

| No. | Substrate | Product | β/α ratio | Conversion |
|---|---|---|---|---|
| 1 | R₁ = 3-Cl-4-methyoxyphenyl | Example 1 | 5:1 | >95% |
| 2 | R₁ = 3-Cl-4-methyoxyphenyl | Example 2 | 9.5:1 | 85% |
| 3 | R₁ = 3-Cl-4-methyoxyphenyl | Example 5 | 5–7:1 | <10% |

$R^3$ is $C_1$–$C_6$ alkyl;

$R^4$ and $R^5$ are each hydrogen; or $R^4$ and $R^5$ taken together form a second bond between C-13 and C-14;

$R^7$ and $R^8$ are each independently hydrogen or $C_1$–$C_6$ alkyl; or $R^7$ and $R^8$ taken together form a cyclopropyl or cyclobutyl ring;

$R^9$ is hydrogen, $C_1$–$C_6$ alkyl, $C_2$–$C_6$ alkenyl, $C_2$–$C_6$ alkynyl, —$(CH_2)_m$—$(C_3$–$C_5)$cycloalkyl or benzyl, wherein m is the integer one to three;

$R^{10}$ is hydrogen or $C_1$–$C_6$ alkyl;

$R^{11}$ is hydrogen, $C_1$–$C_6$ alkyl, phenyl or benzyl;

$R^{14}$ is hydrogen or $C_1$–$C_6$ alkyl;

$R^{50}$ is hydrogen or (=O);

Y is CH, O, NH, SO, $SO_2$ or $(C_1$–$C_3)$alkylamino;

$R^6$ is $C_1$–$C_6$ alkyl, substituted $(C_1$–$C_6)$alkyl, $(C_3$–$C_8)$ cycloalkyl, substituted $(C_3$–$C_8)$cycloalkyl, a heteroaromatic or substituted heteroaromatic group or a group of formula (IA), (IB) or (IC):

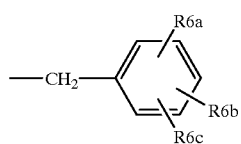
(IA)

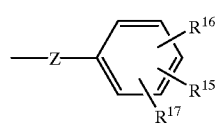
(IB)

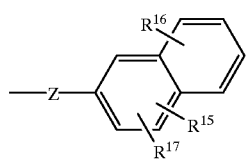
(IC)

$R^{6a}$, $R^{6b}$, and $R^{6c}$ independently are H, halo or $OR^{18}$;

$R^{15}$, $R^{16}$, and $R^{17}$ independently are hydrogen, halo, $(C_1$–$C_6)$ alkyl, $OR^{18}$, O-aryl, $NH_2$, $NR^{18}R^{19}$, $NO_2$, $OPO_4H_2$, $(C_1$–$C_6$alkoxy)phenyl, S-benzyl, $CONH_2$, $CO_2H$, $PO_3H_2$, $SO_2R^{23}$, or Z';

$R^{18}$ and $R^{19}$ independently are hydrogen or $C_1$–$C_6$ alkyl;

$R^{23}$ is hydrogen or $(C_1$–$C_3)$alkyl;

Z is —$(CH_2)_{11}$— or $(C_3$–$C_5)$cycloalkyl;

n is 0, 1, or 2; and

Z' is an aromatic or substituted aromatic group; or a pharmaceutically acceptable salt thereof;

comprising epoxidizing a compound of the formula

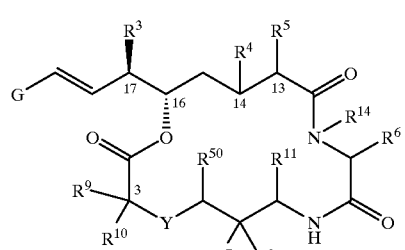
(4)

wherein G, $R^3$, $R^4$, $R^5$, $R^6$, $R^7$, $R^8$, $R^9$, $R^{10}$, $R^{11}$, $R^{14}$ and $R^{50}$ are as defined above and Y is Y' or S; with an oxidant and a chiral ketone to form a compound of formula (I); and optionally forming a pharmaceutically acceptable salt thereof.

2. A process according to claim 1 wherein G is phenyl, para-fluorophenyl, or phenyl substituted with —$CH_2OC(O)$ $(CH_2)_m$·$NH_2$; $R^3$ is methyl; $R^4$ and $R^5$ taken together form a second bond between C-13 and C-14; $R^9$ is $C_1$–$C_6$ alkyl; $R^{10}$ is hydrogen; $R^{11}$ is hydrogen; $R^{14}$ is hydrogen; $R^{50}$ is (=O); Y is O; $R^6$ is a group of the formula (IA).

3. A process according to claim 1 wherein said oxidant is Oxone and said chiral ketone is a compound of the formula

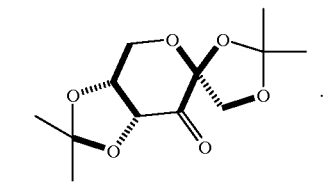

4. A process according to claim 2 wherein G is phenyl.

5. A process according to claim 1 wherein said compound of formula (I) is Cryptophycin 52.

6. A process for preparing a compound of the formula

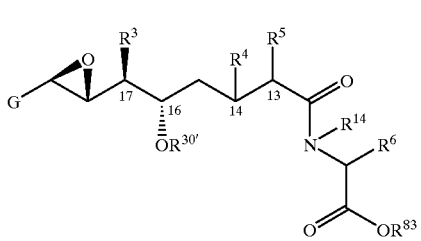
(II)

wherein

G is $C_1$–$C_{12}$ alkyl, $C_2$–$C_{12}$ alkenyl, $C_2$–$C_{12}$ alkynyl, or Ar;

Ar is an aromatic or heteroaromatic group or a substituted aromatic or heteroaromatic group;

$R^3$ is $C_1$–$C_6$ alkyl;

$R^4$ and $R^5$ are each hydrogen; or $R^4$ and $R^5$ taken together form a second bond between C-13 and C-14;

$R^{83}$ is hydrogen, $C_1$–$C_6$ alkyl, trichloroethyl, or —$CH_2SR^{81}$;

$R^{30'}$ is hydrogen, an alcohol protecting group, or a group of the formula

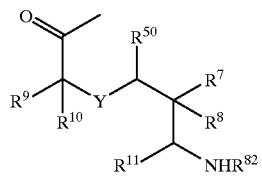

$R^7$ and $R^8$ are each independently hydrogen or $C_1$–$C_6$ alkyl; or $R^7$ and $R^8$ taken together form a cyclopropyl or cyclobutyl ring;

$R^9$ is hydrogen, $C_1$–$C_6$ alkyl, $C_2$–$C_6$ alkenyl, $C_2$–$C_6$ alkynyl, —$(CH_2)_m$—$(C_3$–$C_5)$cycloalkyl or benzyl, wherein m is the integer one to three;

$R^{10}$ is hydrogen or $C_1$–$C_6$ alkyl;

$R^{11}$ is hydrogen, $C_1$–$C_6$ alkyl, phenyl or benzyl;

$R^{14}$ is hydrogen or $C_1$–$C_6$ alkyl;

$R^{50}$ is hydrogen or (=O);

Y is CH, O, $NR^{12}$, S, SO, $SO_2$, wherein $R^{12}$ is H or $C_1$–$C_3$ alkyl;

$R^6$ is $C_1$–$C_6$ alkyl, substituted $(C_1$–$C_6)$alkyl, $(C_3$–$C_8)$cycloalkyl, substituted $(C_3$–$C_8)$cycloalkyl, a heteroaromatic or substituted heteroaromatic group or a group of formula (IA), (IB) or (IC):

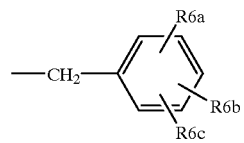

(IA)

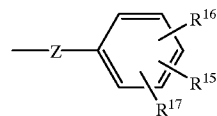

(IB)

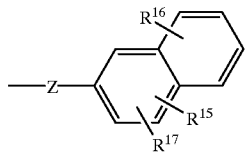

(IC)

$R^{6a}$, $R^{6b}$, and $R^{6c}$ independently are H, $(C_1$–$C_6)$alkyl, halo $NR^{18}R^{19}$ or $OR^{18}$;

$R^{15}$, $R^{16}$, and $R^{17}$ independently are hydrogen, halo, $(C_1$–$C_6)$alkyl, $OR^{18}$, O-aryl, $NH_2$, $NR^{18}R^{19}$, $NO_2$, $OPO_4H_2$, $(C_1$–$C_6$ alkoxy)phenyl, S-benzyl, $CONH_2$, $CO_2H$, $PO_3H_2$, $SO_2R^{23}$, or Z';

$R^{18}$ and $R^{19}$ independently are hydrogen or $C_1$–$C_6$ alkyl;

$R^{23}$ is hydrogen or $(C_1$–$C_3)$alkyl;

Z is —$(CH_2)_n$— or $(C_3$–$C_5)$cycloalkyl;

n is 0, 1, or 2; and

Z' is an aromatic or substituted aromatic group;

$R^{81}$ is $C_1$–$C_6$ alkyl, $C_3$–$C_8$ cycloalkyl, phenyl or benzyl; and $R^{82}$ is a base labile protecting group; or a pharmaceutically acceptable salt thereof; with the proviso that when $R^{83}$ is —$CH_2SR^{81}$, $R^{30}$ is not hydrogen or an alcohol protecting group;

comprising epoxidizing a compound of the formula

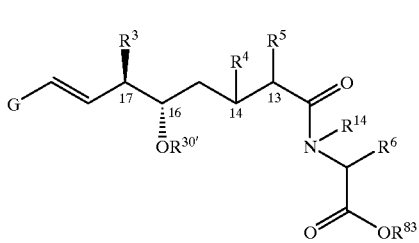

(5)

wherein G, $R^3$, $R^4$, $R^5$, $R^6$, $R^{14}$, $R^{30'}$ and $R^{83}$ are as defined above; with an oxidant and a chiral ketone to form a compound of formula (II); and optionally forming a pharmaceutically acceptable salt thereof.

7. A process according to claim 6 wherein G is phenyl, para-fluorophenyl, or phenyl substituted with —$CH_2OC(O)$$(CH_2)_{m'}NH_2$; $R^3$ is methyl; $R^4$ and $R^5$ taken together form a second bond between C-13 and C-14; $R^9$ is $C_1$–$C_6$ alkyl; $R^{10}$ is hydrogen; $R^{11}$ is hydrogen; $R^{14}$ is hydrogen; $R^{50}$ is (=O); Y is O; $R^6$ is a group of the formula (IA), $R^{30'}$ is hydrogen.

8. A process according to claim 6 wherein said oxidant is Oxone and said chiral ketone is a compound of the formula

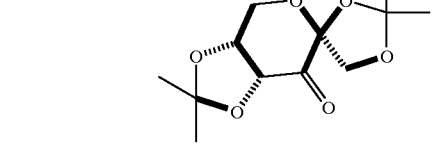

9. A process according to claim 7 wherein G is phenyl and $R^{83}$ is trichloroethyl.

10. A process according to claim 6 wherein said compound of formula (II) is represented by the formula

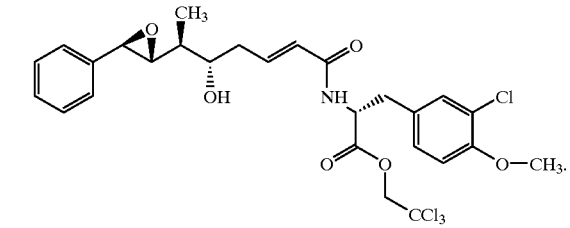

11. A process according to claim 6 further comprising forming a compound of formula (I).

12. A process for preparing a compound of formula (I) according to claim 6, further comprising the steps of:

(a) contacting the compound of formula (II), wherein $R^{30'}$ is hydrogen and $R^{83}$ is a cation, with a thioester forming agent to form a compound of the formula

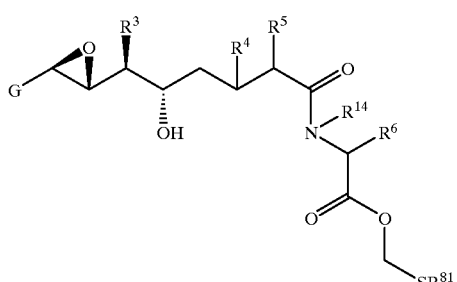

(IIc)

wherein G, $R^3$, $R^4$, $R^5$, $R^6$ and $R^{14}$ are as defined above and $R^{81}$ is $C_1$–$C_6$ alkyl, $C_3$–$C_8$ cycloalkyl, phenyl or benzyl;

(b) coupling a compound of formula (IIc) with a compound of the formula

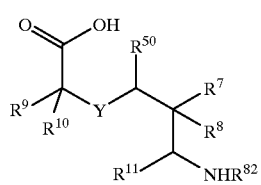

(10a)

wherein $R^7$, $R^8$, $R^9$, $R^{10}$, $R^{11}$ and $R^{50}$ are as defined above and $R^{82}$ is a base labile protecting group, to form a compound of the formula (8)

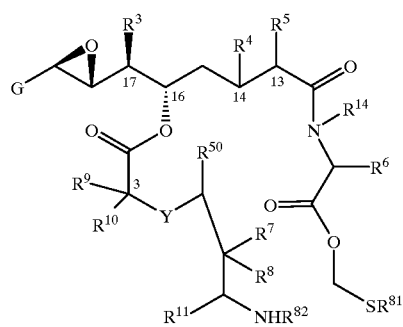

wherein G, $R^3$, $R^4$, $R^5$, $R^6$, $R^7$, $R^8$, $R^9$, $R^{10}$, $R^{11}$, $R^{14}$, $R^{50}$ $R^{81}$, $R^{82}$ and Y are as defined above;

(c) oxidizing a compound of formula (8) with an oxidizing agent to form a compound of the formula

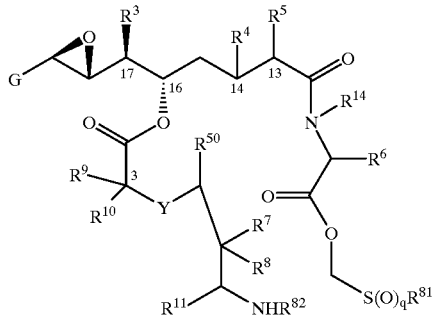

(9)

wherein G, $R^3$, $R^4$, $R^5$, $R^6$, $R^7$, $R^8$, $R^9$, $R^{10}$, $R^{11}$, $R^{14}$, $R^{50}$, $R^{81}$ and $R^{82}$ and Y are as defined above and q is an integer 1 or 2;

(d) deprotecting a compound of formula (9) with a suitable deprotecting agent to form a compound of the formula

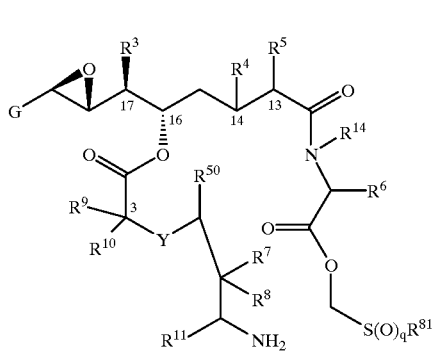

(13)

wherein G, $R^3$, $R^5$, $R^6$, $R^7$, $R^8$, $R^9$, $R^{10}$, $R^{11}$, $R^{14}$, $R^{50}$, Y, q and $R^{81}$ are as defined above; and optionally contacting a compound of formula (10) with a cyclizing agent to form a compound of formula (I); and (e) optionally forming a pharmaceutically acceptable salt of a compound of formula (I).

13. A process according to claim 12 wherein G is phenyl, para-fluorophenyl, or phenyl substituted with —$CH_2OC(O)$ $(CH_2)_{m'}NH_2$; $R^3$ is methyl; $R^4$ and $R^5$ taken together form a second bond between C-13 and C-14; $R^9$ is $C_1$–$C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA); said deprotecting agent is piperidine; said oxidizing agent is Oxone; said oxidant is Oxone and said chiral ketone is a compound of formula (7) and the pH of the epoxidation step is maintained in the range of from about 7.0 to about 11.5.

14. A process according to claim 12 wherein said compound of formula (I) is Cryptophycin 52.

15. A process for preparing a compound of formula (I) according to claim 6, further comprising the steps of:

(a) deprotecting a compound formula (II) wherein $R^{30'}$ is an alcohol protecting group, with a suitable alkoxy deprotecting agent and further carboxy-deprotecting the compound of formula (II) when $R^{83}$ is $C_1$–$C_6$ is alkyl, with a suitable base to form a compound of the formula

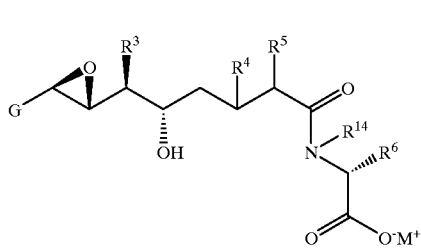
(IIb)

wherein G, $R^3$, $R^4$, $R^5$, $R^6$ and $R^{14}$ are as defined above and $M^+$ is a cation;

(b) contacting the compound of formula (IIb), with a thioester forming agent to form a compound of the formula

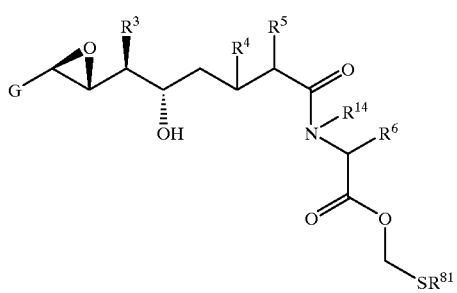
(IIc)

wherein G, $R^3$, $R^4$, $R^5$, $R^6$ and $R^{14}$ are as defined above and $R^{81}$ is $C_1$–$C_6$ alkyl, $C_3$–$C_8$ cycloalkyl, phenyl or benzyl;

(c) coupling a compound of formula (IIc) with a compound of the formula

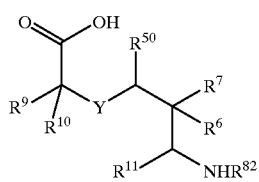
(10a)

wherein $R^7$, $R^8$, $R^9$, $R^{10}$, $R^{11}$ and $R^{50}$ are as defined above and $R^{82}$ is a base labile protecting group, to form a compound of the formula

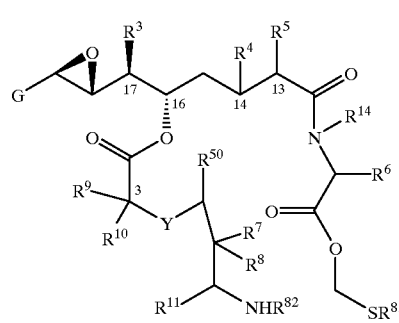
(8)

wherein G, $R^3$, $R^4$, $R^5$, $R^6$, $R^7$, $R^8$, $R^9$, $R^{10}$, $R^{11}$, $R^{14}$, $R^{50}$, $R^{81}$, $R^{82}$ and Y are as defined above;

(d) oxidizing a compound of formula (8) with an oxidizing agent to form a compound of the formula

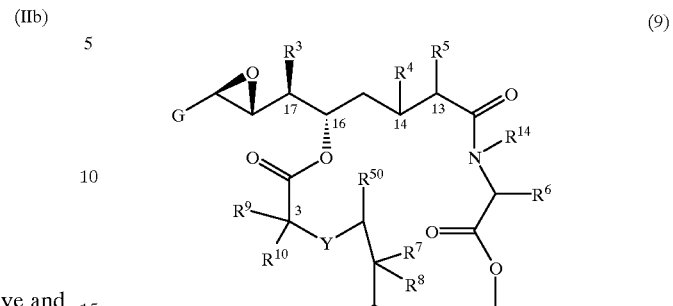
(9)

wherein G, $R^3$, $R^4$, $R^5$, $R^6$, $R^7$, $R^8$, $R^9$, $R^{10}$, $R^{11}$, $R^{14}$, $R^{50}$, $R^{81}$ and $R^{82}$ and Y are as defined above and q is an integer 1 or 2;

(e) deprotecting a compound of formula (9) with a suitable deprotecting agent to form a compound of the formula

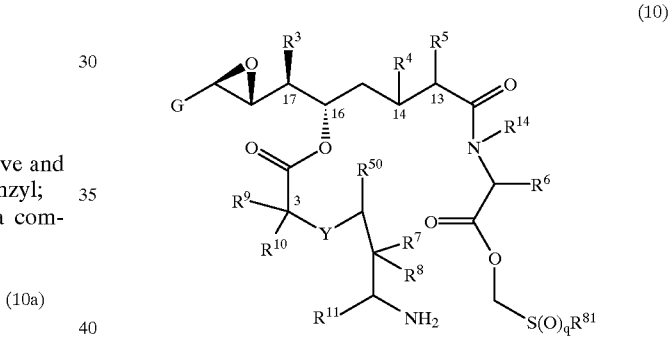
(10)

wherein G, $R^3$, $R^5$, $R^6$, $R^7$, $R^8$, $R^9$, $R^{10}$, $R^{11}$, $R^{14}$, $R^{50}$, Y, q and $R^{81}$ are as defined above; and optionally contacting a compound of formula (10) with a cyclizing agent to form a compound of formula (I); and (f) optionally forming a pharmaceutically acceptable salt of a compound of formula (I).

16. A process according to claim 15 wherein G is phenyl, para-fluorophenyl, or phenyl substituted with —$CH_2OC(O)$ $(CH_2)_{m'}NH_2$; $R^3$ is methyl; $R^4$ and $R^5$ taken together form a second bond between C-13 and C-14; $R^9$ is $C_1$–$C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA); said deprotecting agent is piperidine; said oxidizing agent is Oxone; said oxidant is Oxone and said chiral ketone is a compound of formula (7).

17. A process according to claim 15 wherein said compound of formula (I) is Cryptophycin 52.

18. A process for preparing a compound of formula (I) according to claim 6 further comprising the steps of:

(a) oxidizing a compound of formula (II) wherein $R^{30'}$ is a compound of the formula

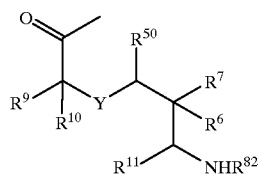

and $R^{83}$ is —$CH_2SR^{81}$, with an oxidizing agent to form a compound of the formula (9)

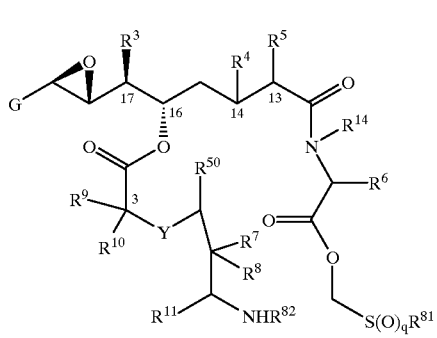

wherein G, $R^3$, $R^4$, $R^5$, $R^6$, $R^7$, $R^8$, $R^9$, $R^{10}$, $R^{11}$, $R^{14}$, $R^{50}$, $R^{81}$ and $R^{82}$ and Y are as defined above and q is an integer 1 or 2;

(b) deprotecting a compound of formula (9) with a suitable deprotecting agent to form a compound of the formula (10)

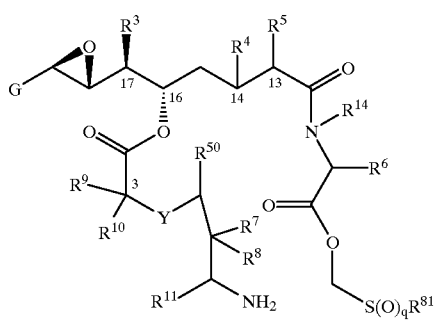

wherein G, $R^3$, $R^5$, $R^6$, $R^7$, $R^8$, $R^9$, $R^{10}$, $R^{11}$, $R^{14}$, $R^{50}$, Y, q and $R^{81}$ are as defined above; and optionally contacting a compound of formula (10) with a cyclizing agent to form a compound of formula (I); and (c) optionally forming a pharmaceutically acceptable salt of a compound of formula (I).

19. A process according to claim 18 wherein G is phenyl, para-fluorophenyl, or phenyl substituted with —$CH_2OC(O)(CH_2)_{m'}NH_2$; $R^3$ is methyl; $R^4$ and $R^5$ taken together form a second bond between C-13 and C-14; $R^9$ is $C_1$–$C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA); said deprotecting agent is piperidine; said oxidizing agent is Oxone; said oxidant is Oxone and said chiral ketone is a compound of formula (7).

20. A process according to claim 18 wherein said compound of formula (I) is Cryptophycin 52.

21. A process for preparing a compound of formula (I) according to claim 6, further comprising the steps of (a) coupling a compound of formula (II), wherein $R^{30'}$ is hydrogen and $R^{83}$ is trichloroethyl, with a compound of the formula (10a)

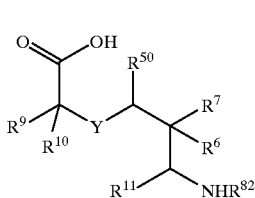

wherein $R^7$, $R^8$, $R^9$, $R^{10}$, $R^{11}$ and $R^{50}$ are as defined above and $R^{82}$ is a base labile protecting group, to form a compound of the formula (18)

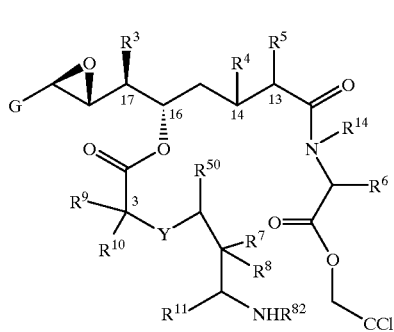

wherein G, $R^3$, $R^4$, $R^5$, $R^6$, $R^7$, $R^8$, $R^9$, $R^{10}$, $R^{11}$, $R^{14}$, $R^{50}$, $R^{82}$ and Y are as defined above;

(b) treating a compound of formula (18) with a suitable base-deprotecting agent to provide a compound of the formula (19)

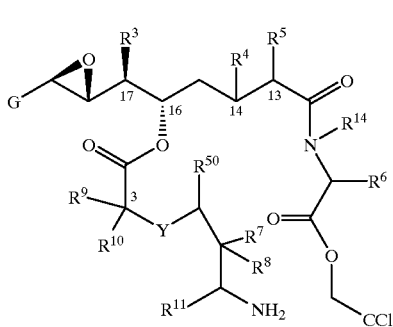

wherein G, $R^3$, $R^4$, $R^5$, $R^6$, $R^7$, $R^8$, $R^9$, $R^{10}$, $R^{11}$, $R^{14}$, $R^{50}$ and Y are as defined above;

(c) cyclizing a compound of formula (19) with a suitable ring-closing agent to provide a compound of formula (I); and (d) optionally forming a pharmaceutically acceptable salt of a compound of formula (I).

22. A process according to claim 21 wherein G is phenyl, para-fluorophenyl, or phenyl substituted with —$CH_2OC(O)(CH_2)_{m'}NH_2$; $R^3$ is methyl; $R^4$ and $R^5$ taken together form a second bond between C-13 and C-14; $R^9$ is $C_1$–$C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA); said oxidizing agent is Oxone; said oxidant is Oxone and said chiral ketone is a compound of formula (7).

23. A process according to claim 21 wherein said compound of formula (I) is Cryptophycin 52.

24. A process for preparing a compound of formula (I) according to claim 6, further comprising the steps of
(a) deprotecting a compound of formula (II) wherein $R^{30'}$ is a compound of the formula

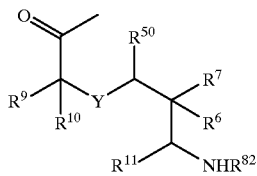

and $R^{83}$ is trichloroethyl, with a suitable base-deprotecting agent to form a compound of the formula

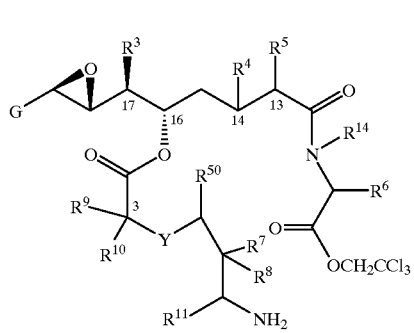

(19)

wherein G, $R^3$, $R^4$, $R^5$, $R^6$ and $R^{14}$ are as defined above;
(b) cyclizing a compound of formula (19) with a suitable ring-closing agent to provide a compound of formula (I); and
(c) optionally forming a pharmaceutically acceptable salt of a compound of formula (I).

25. A process according to claim 24 wherein G is phenyl, para-fluorophenyl, or phenyl substituted with —CH$_2$OC(O)(CH$_2$)$_m$NH$_2$; $R^3$ is methyl; $R^4$ and $R^5$ taken together form a second bond between C-13 and C-14; $R^9$ is C$_1$–C$_6$ alkyl; $R^{10}$ is hydrogen; $R^{11}$ is hydrogen; $R^{14}$ is hydrogen; $R^{50}$ is (=O); Y is O; and $R^6$ is a group of the formula (IA); said oxidizing agent is Oxone; said oxidant is Oxone and said chiral ketone is a compound of formula (7).

26. A process according to claim 24 wherein said compound of formula (I) is Cryptophycin 52.

27. A compound of the formula

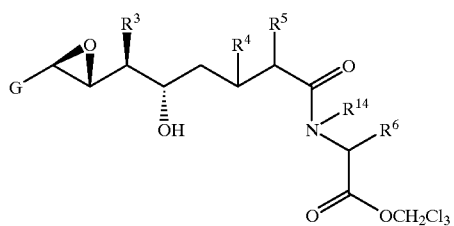

(IId)

wherein
G is C$_1$–C$_{12}$ alkyl, C$_2$–C$_{12}$ alkenyl, C$_2$–C$_{12}$ alkynyl, or Ar;

Ar is an aromatic or heteroaromatic group or a substituted aromatic or heteroaromatic group;
$R^3$ is C$_1$–C$_6$ alkyl;
$R^4$ and $R^5$ are each hydrogen; or $R^4$ and $R^5$ taken together form a second bond between C-13 and C-14;
$R^{14}$ is hydrogen or C$_1$–C$_6$ alkyl;
$R^6$ is C$_1$–C$_6$ alkyl, substituted (C$_1$–C$_6$)alkyl, (C$_3$–C$_8$) cycloalkyl, substituted (C$_3$–C$_8$)cycloalkyl, a heteroaromatic or substituted heteroaromatic group or a group of formula (IA), (IB) or (IC):

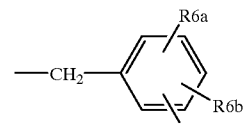

(IA)

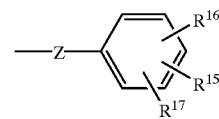

(IB)

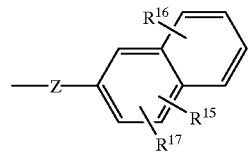

(IC)

$R^{6a}$, $R^{6b}$, and $R^{6c}$ independently are H, halo or OR$^{18}$;
$R^{15}$, $R^{16}$, and $R^{17}$ independently are hydrogen, halo, (C$_1$–C$_6$)alkyl, OR$^{18}$, O-aryl, NH$_2$, NR$^{18}$R$^{19}$, NO$_2$, OPO$_4$H$_2$, (C$_1$–C$_6$ alkoxy)phenyl, S-benzyl, CONH$_2$, CO$_2$H, PO$_3$H$_2$, SO$_2$R$^{23}$, or Z';
$R^{18}$ and $R^{19}$ independently are hydrogen or C$_1$–C$_6$ alkyl;
$R^{23}$ is hydrogen or (C$_1$–C$_3$)alkyl;
Z is —(CH$_2$)$_n$— or (C$_3$–C$_5$)cycloalkyl;
n is 0, 1, or 2; and
Z' is an aromatic or substituted aromatic group; or a pharmaceutically acceptable salt thereof.

28. A compound according to claim 27 wherein G is phenyl, para-fluorophenyl, or phenyl substituted with —CH$_2$OC(O)(CH$_2$)$_m$NH$_2$; $R^3$ is methyl; $R^4$ and $R^5$ taken together form a second bond between C-13 and C-14; $R^{14}$ is hydrogen; and $R^6$ is a group of the formula (IA).

29. A compound according to claim 27 wherein said compound is represented by the formula

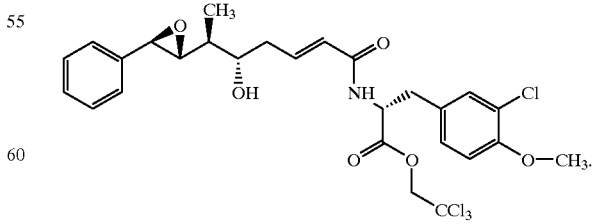

30. A compound of the formula (18)

wherein
G is $C_1$–$C_{12}$ alkyl, $C_2$–$C_{12}$ alkenyl, $C_2$–$C_{12}$ alkynyl, or Ar;
Ar is an aromatic or heteroaromatic group or a substituted aromatic or heteroaromatic group;
$R^3$ is $C_1$–$C_6$ alkyl;
$R^4$ and $R^5$ are each hydrogen; or $R^4$ and $R^5$ taken together form a second bond between C-13 and C-14;
$R^7$ and $R^8$ are each independently hydrogen or $C_1$–$C_6$ alkyl; or
$R^7$ and $R^8$ taken together form a cyclopropyl or cyclobutyl ring;
$R^9$ is hydrogen, $C_1$–$C_6$ alkyl, $C_2$–$C_6$ alkenyl, $C_2$–$C_6$ alkynyl, —$(CH_2)_m$—$(C_3$–$C_5)$cycloalkyl or benzyl, wherein m is the integer one to three;
$R^{10}$ is hydrogen or $C_1$–$C_6$ alkyl;
$R^{11}$ is hydrogen, $C_1$–$C_6$ alkyl, phenyl or benzyl;
$R^{14}$ is hydrogen or $C_1$–$C_6$ alkyl;
$R^{50}$ is hydrogen or (=O);
Y is CH, O, NH, S, SO, $SO_2$ or $(C_1$–$C_3)$alkylamino;
$R^6$ is $C_1$–$C_6$ alkyl, substituted $(C_1$–$C_6)$alkyl, $(C_3$–$C_8)$cycloalkyl, substituted $(C_3$–$C_8)$cycloalkyl, a heteroaromatic or substituted heteroaromatic group or a group of formula (IA), (IB) or (IC):

(IA)

(IB)

(IC)

$R^{6a}$, $R^{6b}$, and $R^{6c}$ independently are H, halo or $OR^{18}$;
$R^{15}$, $R^{16}$, and $R^{17}$ independently are hydrogen, halo, $(C_1$–$C_6)$alkyl, $OR^{18}$, O-aryl, $NH_2$, $NR^{19}R^{19}$, $NO_2$, $OPO_4H_2$, $(C_1$–$C_6$ alkoxy)phenyl, S-benzyl, $CONH_2$, $CO_2H$, $PO_3H_2$, $SO_2R^{23}$, or Z';

$R^{18}$ and $R^{19}$ independently are hydrogen or $C_1$–$C_6$ alkyl;
$R^{23}$ is hydrogen or $(C_1$–$C_3)$alkyl;
Z is —$(CH_2)_n$— or $(C_3$–$C_5)$cycloalkyl;
n is 0, 1, or 2;
Z' is an aromatic or substituted aromatic group; and
$R^{82}$ is a base labile protecting group; or a pharmaceutically acceptable salt thereof.

31. A compound according to claim 30 wherein G is phenyl, para-fluorophenyl, or phenyl substituted with —$CH_2OC(O)(CH_2)_{m'}NH_2$; $R^3$ is methyl; $R^4$ and $R^5$ taken together form a second bond between C-13 and C-14; $R^9$ is $C_1$–$C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA).

32. A compound according to claim 30 wherein said compound is represented by the formula 33. A compound of the formula (19)

wherein
G is $C_1$–$C_{12}$ alkyl, $C_2$–$C_{12}$ alkenyl, $C_2$–$C_{12}$ alkynyl, or Ar;
Ar is an aromatic or heteroaromatic group or a substituted aromatic or heteroaromatic group;
$R^3$ is $C_1$–$C_6$ alkyl;
$R^4$ and $R^5$ are each hydrogen; or $R^4$ and $R^5$ taken together form a second bond between C-13 and C-14;
$R^7$ and $R^8$ are each independently hydrogen or $C_1$–$C_6$ alkyl; or
$R^7$ and $R^8$ taken together form a cyclopropyl or cyclobutyl ring;
$R^9$ is hydrogen, $C_1$–$C_6$ alkyl, $C_2$–$C_6$ alkenyl, $C_2$–$C_6$ alkynyl, —$(CH_2)_m$—$(C_3$–$C_5)$cycloalkyl or benzyl, wherein m is the integer one to three;
$R^{10}$ is hydrogen or $C_1$–$C_6$ alkyl;
$R^{11}$ is hydrogen, $C_1$–$C_6$ alkyl, phenyl or benzyl;
$R^{14}$ is hydrogen or $C_1$–$C_6$ alkyl;
$R^{50}$ is hydrogen or (=O);
Y is CH, O, NH, S, SO, $SO_2$ or $(C_1$–$C_3)$alkylamino;
$R^6$ is $C_1$–$C_6$ alkyl, substituted $(C_1$–$C_6)$alkyl, $(C_3$–$C_8)$cycloalkyl, substituted $(C_3$–$C_8)$cycloalkyl, a heteroaromatic or substituted heteroaromatic group or a group of formula (IA), (IB) or (IC):

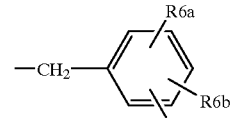
(IA)

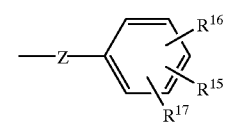
(IB)

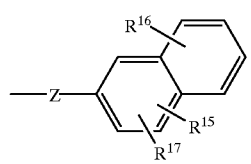
(IC)

$R^{6a}$, $R^{6b}$, and $R^{6c}$ independently are H, halo or $OR^{18}$;

$R^{15}$, $R^{16}$, and $R^{17}$ independently are hydrogen, halo, $(C_1-C_6)$alkyl, $OR^{18}$, O-aryl, $NH_2$, $NR^{18}R^{19}$, $NO_2$, $OPO_4H_2$, $(C_1-C_6$ alkoxy)phenyl, S-benzyl, $CONH_2$, $CO_2H$, $PO_3H_2$, $SO_2R^{23}$, or Z';

$R^{18}$ and $R^{19}$ independently are hydrogen or $C_1-C_6$ alkyl;

$R^{23}$ is hydrogen or $(C_1-C_3)$alkyl;

Z is $-(CH_2)_n-$ or $(C_3-C_5)$cycloalkyl;

n is 0, 1, or 2; and

Z' is an aromatic or substituted aromatic group; or a pharmaceutically acceptable salt thereof.

34. A compound according to claim 33 wherein G is phenyl, para-fluorophenyl, or phenyl substituted with $-CH_2OC(O)(CH_2)_{m'}NH_2$; $R^3$ is methyl; $R^4$ and $R^5$ taken together form a second bond between C-13 and C-14; $R^9$ is $C_1-C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA).

35. A compound according to claim 33 wherein said compound is represented by the formula

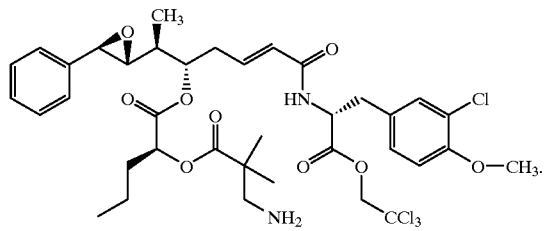

36. A process for preparing a compound of the formula

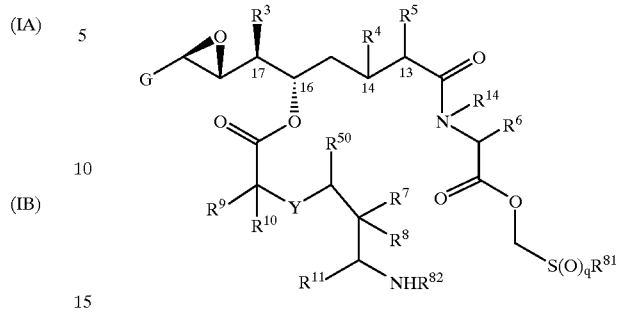
(9)

wherein

G is $C_1-C_{12}$ alkyl, $C_2-C_{12}$ alkenyl, $C_2-C_{12}$ alkynyl, or Ar;

Ar is an aromatic or heteroaromatic group or a substituted aromatic or heteroaromatic group;

$R^3$ is $C_1-C_6$ alkyl;

$R^4$ and $R^5$ are each hydrogen; or $R^4$ and $R^5$ taken together form a second bond between C-13 and C-14;

$R^7$ and $R^8$ are each independently hydrogen or $C_1-C_6$ alkyl; or $R^7$ and $R^8$ taken together form a cyclopropyl or cyclobutyl ring;

$R^9$ is hydrogen, $C_1-C_6$ alkyl, $C_2-C_6$ alkenyl, $C_2-C_6$ alkynyl, $-(CH_2)_m-(C_3-C_5)$cycloalkyl or benzyl, wherein m is the integer one to three;

$R^{10}$ is hydrogen or $C_1-C_6$ alkyl;

$R^{11}$ is hydrogen, $C_1-C_6$ alkyl, phenyl or benzyl;

$R^{14}$ is hydrogen or $C_1-C_6$ alkyl;

$R^{50}$ is hydrogen or (=O);

Y is CH, O, $NR^{12}$, S, SO, $SO_2$, wherein $R^{12}$ is H or $C_1-C_3$ alkyl;

$R^6$ is $C_1-C_6$ alkyl, substituted $(C_1-C_6)$alkyl, $(C_3-C_8)$ cycloalkyl, substituted $(C_3-C_8)$cycloalkyl, a heteroaromatic or substituted heteroaromatic group or a group of formula (IA), (IB) or (IC):

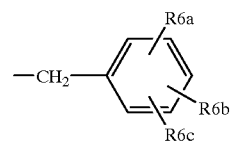
(IA)

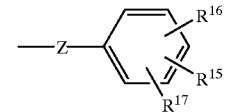
(IB)

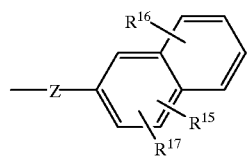
(IC)

$R^{6a}$, $R^{6b}$, and $R^{6c}$ independently are H, $(C_1-C_6)$alkyl, halo $NR^{18}R^{19}$ or $OR^{18}$;

$R^{15}$, $R^{16}$, and $R^{17}$ independently are hydrogen, halo, $(C_1-C_6)$alkyl, $OR^{18}$, O-aryl, $NH_2$, $NR^{18}R^{19}$, $NO_2$, $OPO_4H_2$, $(C_1-C_6$ alkoxy)phenyl, S-benzyl, $CONH_2$, $CO_2H$, $PO_3H_2$, $SO_2R^{23}$, or Z';

$R^{18}$ and $R^{19}$ independently are hydrogen or $C_1-C_6$ alkyl;

$R^{23}$ is hydrogen or $(C_1-C_3)$alkyl;

$R^{81}$ is $C_1-C_6$ alkyl, $C_3-C_8$ cycloalkyl, phenyl or benzyl;

$R^{82}$ is a base labile protecting group;

Z is —$(CH_2)_n$— or $(C_3-C_5)$cycloalkyl;

n is 0, 1, or 2;

q is an integer 1 or 2; and

Z' is an aromatic or substituted aromatic group; or a pharmaceutically acceptable salt thereof;

comprising oxidizing a compound of the formula

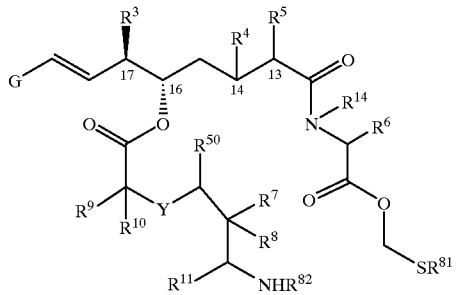

(11)

wherein G, $R^3$, $R^4$, $R^5$, $R^6$, $R^7$, $R^8$, $R^9$, $R^{10}$, $R^{11}$, $R^{14}$, $R^{50}$, $R^{81}$, $R^{82}$ and Y are as defined above, with an oxidizing agent to form a compound of formula (9) and optionally forming a pharmaceutically acceptable salt of a compound of formula (9).

37. A process according to claim 36 wherein G is phenyl, para-fluorophenyl, or phenyl substituted with —$CH_2OC(O)$ $(CH_2)_{m'}NH_2$; $R^3$ is methyl; $R^4$ and $R^5$ taken together form a second bond between C-13 and C-14; $R^9$ is $C_1-C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA) and the oxidizing agent is Oxone.

38. A process for preparing a compound of formula (I) according to claim 36, further comprising the steps of:

(a) deprotecting a compound of formula (9) with a suitable deprotecting agent to form a compound of the formula (10)

wherein G, $R^3$, $R^5$, $R^6$, $R^7$, $R^8$, $R^9$, $R^{10}$, $R^{11}$, $R^{14}$, $R^{50}$, Y, q and $R^{81}$ are as defined above; and optionally contacting a compound of formula (10) with a cyclizing agent to form a compound of formula (I); and (b) optionally forming a pharmaceutically acceptable salt of a compound of formula (I).

39. A process according to claim 38 wherein G is phenyl, para-fluorophenyl, or phenyl substituted with —$CH_2OC(O)$ $(CH_2)_{m'}NH_2$; $R^3$ is methyl; $R^4$ and $R^5$ taken together form a second bond between C-13 and C-14; $R^9$ is $C_1-C_6$ alkyl; $R^{10}$ is hydrogen; $R^{11}$ is hydrogen; $R^{14}$ is hydrogen; $R^{50}$ is (=O); Y is O; and $R^6$ is a group of the formula (IA); said deprotecting agent is piperidine; said oxidizing agent is Oxone; said oxidant is Oxone and said chiral ketone is a compound of formula (7).

40. A process according to claim 38 wherein said compound of formula (I) is Cryptophycin 52.

* * * * *